(12) United States Patent
English et al.

(10) Patent No.: US 8,865,967 B2
(45) Date of Patent: Oct. 21, 2014

(54) DEFENSIN VARIANTS AND METHODS OF USE

(75) Inventors: James J. English, San Ramon, CA (US); Susan L. Grant, Urbandale, IA (US); Jeffrey S. Pollack, Redwood City, CA (US); Julia L. Ritland, Hubbard, IA (US); Gary A. Sandahl, West Des Moines, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 542 days.

(21) Appl. No.: 13/213,158

(22) Filed: Aug. 19, 2011

(65) Prior Publication Data

US 2012/0054911 A1 Mar. 1, 2012

Related U.S. Application Data

(60) Provisional application No. 61/376,029, filed on Aug. 23, 2010.

(51) Int. Cl.
| | | |
|---|---|---|
| *C07K 14/415* | (2006.01) | |
| *A01N 63/00* | (2006.01) | |
| *C07H 21/02* | (2006.01) | |
| *C12N 15/00* | (2006.01) | |
| *A01H 5/00* | (2006.01) | |
| *A01H 1/00* | (2006.01) | |
| *C12N 15/82* | (2006.01) | |
| *A01N 37/46* | (2006.01) | |

(52) U.S. Cl.
CPC ........ *C12N 15/8279* (2013.01); *C12N 15/8282* (2013.01); *C07K 14/415* (2013.01); *A01N 37/46* (2013.01)
USPC ....... 800/279; 800/301; 435/320.1; 536/23.1; 424/93.2; 530/324

(58) Field of Classification Search
None
See application file for complete search history.

(56) References Cited

U.S. PATENT DOCUMENTS

2005/0273881 A1* 12/2005 Simmons et al. ............. 800/279
2012/0124699 A1* 5/2012 English et al. ................ 800/279

FOREIGN PATENT DOCUMENTS

WO 03/000863 A2 1/2003

OTHER PUBLICATIONS

French et al. What is a conservative substitution? 1983. J. Mol. Evol. 19:171-175.*
Stotz et al. Plant defensins, Defense, development and application. 2009. Plant Signal. Behav. 4(11):1010-1012.*
EBI Accession No. GSN:ADA23022 "*Picramnia pentandra* defensin encoding cDNA SEQ ID No. 214.", XP0023665437 ; Nov. 20, 2003.
EBI Accession No. GSP: ADA23023, "*Picramnia pentandra* defensin protein SEQ ID No. 215", XP002665438, Nov. 20, 2003.
EBI Accession No. GSN:ADA23024, "*Picramnia pentandra* defensin mature protein SEQ ID No. 216.", XP002665439, Nov. 20, 2003.
Patent Cooperation Treaty, International Search Report, 2345-PCT, PCT/US2011/048364; Aug. 19, 2011.

* cited by examiner

*Primary Examiner* — Russell Kallis
*Assistant Examiner* — Jeffrey Bolland
(74) *Attorney, Agent, or Firm* — Pioneer Hi-Bred Int'l

(57) ABSTRACT

Compositions and methods for protecting a plant from a pathogen, particularly a fungal pathogen, are provided. Compositions include amino acid sequences, and variants and fragments thereof, for novel variants of antipathogenic polypeptides generated through DNA shuffling that exhibit improved antipathogenic activity. Polynucleotides that encode the antipathogenic polypeptides are also provided. A method for inducing pathogen resistance in a plant using the polynucleotides disclosed herein is further provided. Compositions comprising an antipathogenic polypeptide or a microorganism comprising an antipathogenic polynucleotide of the invention in combination with a carrier and methods of using these compositions to protect a plant from a pathogen are further provided. Plants, plant cells, seeds, and microorganisms comprising an antipathogenic polynucleotide or polypeptide of the invention are also disclosed.

15 Claims, 1 Drawing Sheet

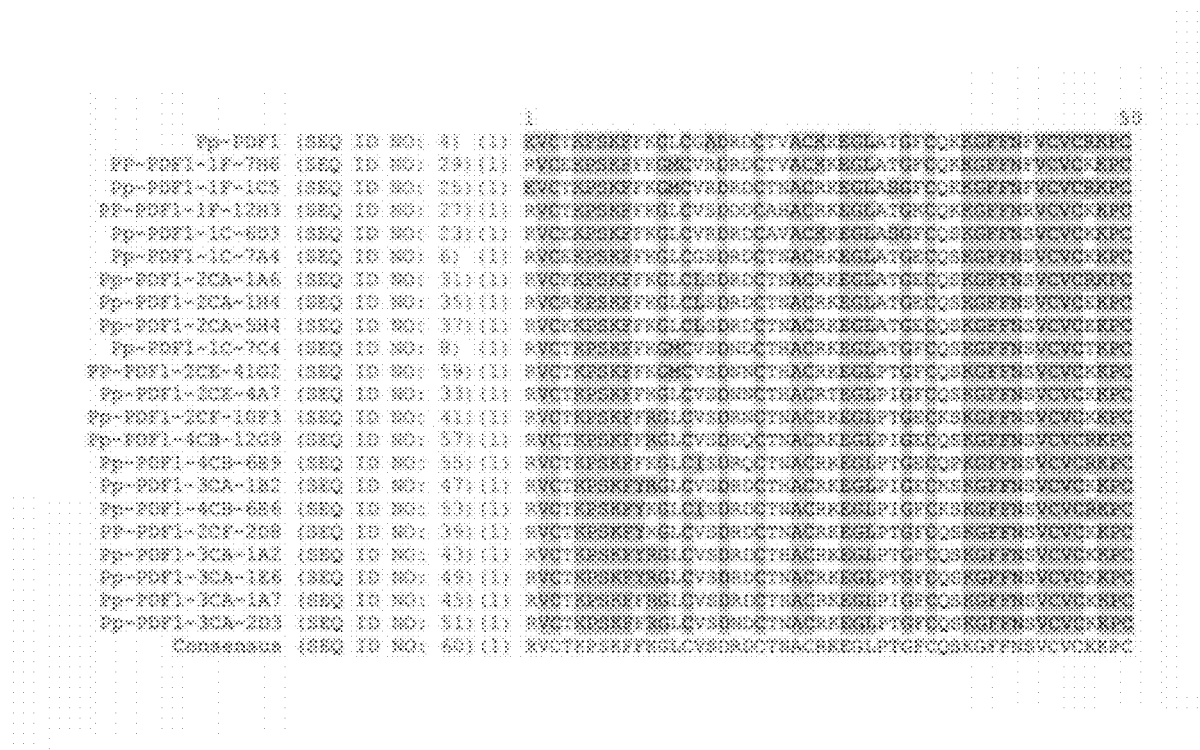

US 8,865,967 B2

DEFENSIN VARIANTS AND METHODS OF USE

CROSS-REFERENCE TO RELATED APPLICATIONS

This application claims priority to U.S. Provisional Application No. 61/376,029, filed Aug. 23, 2010, which is hereby incorporated herein in its entirety by reference.

FIELD OF THE INVENTION

The present invention relates to polypeptides having antipathogenic activity and polynucleotides that encode the same. Methods of the invention utilize these antipathogenic polynucleotides and polypeptides to control plant pathogens and to increase pathogen resistance in plants.

BACKGROUND OF THE INVENTION

Plant diseases are often a serious limitation on agricultural productivity and therefore have influenced the history and development of agricultural practices. A variety of pathogens are responsible for plant diseases, including fungi, bacteria, viruses, and nematodes. Among the causal agents of infectious diseases of crop plants, however, fungi are the most economically important group of plant pathogens and are responsible for huge annual losses of marketable food, fiber, and feed.

Incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Consumers and government regulators alike are becoming increasingly concerned with the environmental hazards associated with the production and use of synthetic agrochemicals for protecting plants from pathogens. Because of such concerns, regulators have banned or limited the use of some of the more hazardous chemicals. The incidence of fungal diseases has been controlled to some extent by breeding resistant crops. Traditional breeding methods, however, are time-consuming and require continuous effort to maintain disease resistance as pathogens evolve. See, for example, Grover and Gowthaman (2003) *Curr. Sci.* 84:330-340. Thus, there is a substantial interest in developing novel alternatives for the control of plant pathogens that possess a lower risk of pollution and environmental hazards than is characteristic of traditional agrochemical-based methods and that are less cumbersome than conventional breeding techniques.

Recently, agricultural scientists have developed crop plants with enhanced pathogen resistance by genetically engineering plants to express antipathogenic proteins. A continuing effort to identify antipathogenic agents and to genetically engineer disease-resistant plants is underway.

Thus, in light of the significant impact of plant pathogens, particularly fungal pathogens, on the yield and quality of crops, new compositions and methods for protecting plants from pathogens are needed.

BRIEF SUMMARY OF THE INVENTION

Compositions and methods for protecting a plant from a pathogen are provided. The compositions include novel nucleotide and amino acid sequences for antipathogenic, particularly antifungal, polypeptides. The presently disclosed polypeptides display antipathogenic activity against plant fungal pathogens. Polynucleotides comprising nucleotide sequences that encode the presently disclosed antipathogenic polypeptides are further provided. The polypeptides and nucleotide sequences encoding the same were identified through the use of DNA shuffling. In some embodiments, the antifungal polypeptides display an improved antipathogenic activity when compared to the parent polypeptide used in the DNA shuffling event that yielded the novel antipathogenic polypeptide-encoding sequence. Compositions also include expression cassettes comprising a polynucleotide that encodes an antipathogenic polypeptide disclosed herein. Plants, plant cells, seeds, and microorganisms comprising the presently disclosed polynucleotides and polypeptides are further provided.

The compositions are useful in methods directed to inducing pathogen resistance, particularly fungal resistance, in plants. In particular embodiments, the methods comprise introducing into a plant at least one polynucleotide that encodes an antipathogenic polypeptide. As a result, the antipathogenic polypeptide is expressed in the plant, and the pathogen is exposed to the preferred protein at the site of pathogen attack, thereby leading to increased pathogen resistance. A tissue-preferred promoter may be used to drive expression of an antipathogenic protein in specific plant tissues that are particularly vulnerable to pathogen attack, such as, for example, the roots, leaves, stalks, vascular tissues, and seeds. Pathogen-inducible promoters may also be used to drive the expression of an antipathogenic protein at or near the site of pathogen infection.

Further provided are antipathogenic compositions and formulations and methods for their use in protecting a plant from a pathogen, particularly a fungal pathogen. In some embodiments, compositions comprise an antipathogenic polypeptide or a microorganism comprising a polynucleotide encoding an antipathogenic polypeptide in combination with a carrier. Methods of using these compositions to protect a plant from a pathogen comprise applying the antipathogenic composition to the environment of the plant pathogen by, for example, spraying, dusting, broadcasting, or seed coating. The presently disclosed methods and compositions find use in protecting plants from pathogens, including fungal pathogens, viruses, nematodes, and the like.

The following embodiments are encompassed by the present invention:

1. An isolated polypeptide comprising an amino acid sequence selected from the group consisting of:
   (a) the amino acid sequence set forth in SEQ ID NO: 6, 8, 10, or 12; and
   (b) an amino acid sequence having at least 85% sequence identity to SEQ ID NO: 6, 8, 10, or 12, wherein said polypeptide has antipathogenic activity.

2. The isolated polypeptide of embodiment 1, wherein said polypeptide has an amino acid sequence having at least 85% sequence identity to SEQ ID NO: 6, 8, 10, or 12, and wherein said amino acid sequence has at least one of the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

3. The isolated polypeptide of embodiment 1 or embodiment 2, wherein said polypeptide has antifungal activity.

4. The isolated polypeptide of embodiment 3, wherein said polypeptide has improved antifungal activity when compared to a polypeptide comprising the amino acid sequence set forth in SEQ ID NO: 2 or 4.

5. The isolated polypeptide of embodiment 2, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

6. An isolated polynucleotide comprising a nucleotide sequence selected from the group consisting of:
  (a) the nucleotide sequence set forth in SEQ ID NO: 3, 5, 7, or 9;
  (b) a nucleotide sequence encoding an amino acid sequence comprising SEQ ID NO: 6, 8, 10, or 12;
  (c) a nucleotide sequence having at least 90% sequence identity to SEQ ID NO: 5, 7, 9, or 11, wherein said polynucleotide encodes a polypeptide having antipathogenic activity; and
  (d) a nucleotide sequence encoding an amino acid sequence having at least 85% sequence identity to SEQ ID NO: 6, 8, 10, or 12, wherein said polynucleotide encodes a polypeptide having antipathogenic activity.

7. The isolated polynucleotide of embodiment 6, wherein said polynucleotide encodes a polypeptide having an amino acid sequence having at least 85% sequence identity to SEQ ID NO: 6, 8, 10, or 12, wherein said polynucleotide encodes a polypeptide having antipathogenic activity, and wherein said amino acid sequence has at least one of the amino acid residues selected from the group consisting of:
  (a) the arginine (Arg) residue at the position corresponding to residue 1 of SEQ ID NO: 6, 8, 10, or 12;
  (b) the serine (Ser) residue at the position corresponding to residue 16 of SEQ ID NO: 6, 8, 10, or 12;
  (c) the arginine (Arg) residue at the position corresponding to residue 25 of SEQ ID NO: 6, 8, 10, or 12;
  (d) the serine (Ser) residue at the position corresponding to residue 36 of SEQ ID NO: 6, 8, 10, or 12; and
  (e) the serine (Ser) residue at the position corresponding to residue 42 of SEQ ID NO: 6, 8, 10, or 12.

8. The isolated polynucleotide of embodiment 6, wherein said polynucleotide encodes a polypeptide having antifungal activity.

9. The isolated polynucleotide of embodiment 8, wherein said polypeptide has improved antifungal activity when compared to a polypeptide comprising the amino acid sequence set forth in SEQ ID NO: 2 or 4.

10. The isolated polynucleotide of embodiment 8, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

11. An expression cassette comprising the polynucleotide of any one of embodiments 6-10.

12. The expression cassette of embodiment 11, wherein said polynucleotide is operably linked to a promoter that drives expression in a plant.

13. The expression cassette of embodiment 11, wherein said polynucleotide is operably linked to a promoter that drives expression in a microorganism.

14. A host cell comprising the polynucleotide of any one of embodiments 6-10.

15. A host cell comprising the expression cassette of embodiment 11.

16. A plant comprising a heterologous polynucleotide operably linked to a promoter that drives expression in the plant, wherein said heterologous polynucleotide comprises a nucleotide sequence selected from the group consisting of:
  (a) the nucleotide sequence set forth in SEQ ID NO: 5, 7, 9, or 11;
  (b) a nucleotide sequence encoding an amino acid sequence comprising SEQ ID NO: 6, 8, 10, or 12;
  (c) a nucleotide sequence having at least 90% sequence identity to SEQ ID NO: 5, 7, 9, or 11, wherein said polynucleotide encodes a polypeptide having antipathogenic activity; and
  (d) a nucleotide sequence encoding an amino acid sequence having at least 85% sequence identity to SEQ ID NO: 6, 8, 10, or 12, wherein said polynucleotide encodes a polypeptide having antipathogenic activity.

17. The plant of embodiment 16, wherein said polynucleotide encodes a polypeptide having an amino acid sequence having at least 85% sequence identity to SEQ ID NO: 6, 8, 10, or 12, wherein said polynucleotide encodes a polypeptide having antipathogenic activity, and wherein said amino acid sequence has at least one of the amino acid residues selected from the group consisting of:
  (a) the arginine (Arg) residue at the position corresponding to residue 1 of SEQ ID NO: 6, 8, 10, or 12;
  (b) the serine (Ser) residue at the position corresponding to residue 16 of SEQ ID NO: 6, 8, 10, or 12;
  (c) the arginine (Arg) residue at the position corresponding to residue 25 of SEQ ID NO: 6, 8, 10, or 12;
  (d) the serine (Ser) residue at the position corresponding to residue 36 of SEQ ID NO: 6, 8, 10, or 12; and
  (e) the serine (Ser) residue at the position corresponding to residue 42 of SEQ ID NO: 6, 8, 10, or 12.

18. The plant of embodiment 16, wherein said polynucleotide encodes a polypeptide having antifungal activity.

19. The plant of embodiment 18, wherein said polypeptide has improved antifungal activity when compared to a polypeptide comprising the amino acid sequence set forth in SEQ ID NO: 2 or 4.

20. The plant of embodiment 18, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

21. The plant of any one of embodiments 16-20, wherein said nucleotide sequence is optimized for expression in a plant.

22. The plant of any one of embodiments 16-20, wherein said plant is a plant part selected from the group consisting of a cell, a seed, and a grain.

23. The plant of any one of embodiments 16-20, wherein said plant is a monocot.

24. The plant of embodiment 23, wherein said monocot is maize, sugarcane, wheat, rice, barley, sorghum, or rye.

25. The plant of any one of embodiments 16-20, wherein said plant is a dicot.

26. The plant of embodiment 25, wherein the dicot is soybean, *Brassica*, sunflower, cotton, or alfalfa.

27. The plant of any one of embodiments 16-20, wherein said polynucleotide is stably incorporated into the genome of the plant.

28. The plant of any one of embodiments 16-20, wherein said plant displays increased resistance to a plant pathogen.

29. The plant of embodiment 28, wherein said plant pathogen is a fungus.

30. The plant of embodiment 29, wherein said fungus is at least one of *Colletotrichum graminocola* and *Fusarium graminearum*.

31. The plant of any one of embodiments 16-20, wherein said promoter is a tissue-preferred promoter.

32. The plant of embodiment 31, wherein said tissue-preferred promoter is selected from the group consisting of a leaf-preferred promoter, a root-preferred promoter, a seed-preferred promoter, a stalk-preferred promoter, and a vascular tissue-preferred promoter.

33. The plant of any one of embodiments 16-20, wherein said promoter is a pathogen-inducible promoter.

34. A transformed seed of the plant of any one of embodiments 16-33.

35. A method of enhancing plant pathogen resistance in a plant, said method comprising providing to said plant a polypeptide selected from the group consisting of:
   (a) a polypeptide comprising the amino acid sequence set forth in SEQ ID NO: 6, 8, 10, or 12; and
   (b) a polypeptide comprising an amino acid sequence having at least 85% sequence identity to SEQ ID NO: 6, 8, 10, or 12, wherein said polypeptide has antipathogenic activity.

36. The method of embodiment 35, wherein said polypeptide has an amino acid sequence having at least 85% sequence identity to SEQ ID NO: 6, 8, 10, or 12, and wherein said amino acid sequence has at least one of the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

37. The method of embodiment 35, wherein said polypeptide has antifungal activity.

38. The method of embodiment 37, wherein said polypeptide has improved antifungal activity when compared to a polypeptide comprising the amino acid sequence set forth in SEQ ID NO: 2 or 4.

39. The method of embodiment 37, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

40. The method of any one of embodiments 35-39, wherein said plant is a plant part selected from the group consisting of a cell, a seed, and a grain.

41. The method of any one of embodiments 35-39, wherein said plant is a monocot.

42. The method of embodiment 41, wherein said monocot is maize, sugarcane, wheat, rice, barley, sorghum, or rye.

43. The method of any one of embodiments 35-39, wherein said plant is a dicot.

44. The method of embodiment 43, wherein said dicot is soybean, *Brassica*, sunflower, cotton, or alfalfa.

45. The method of any one of embodiments 35-39, wherein said plant pathogen is a fungus.

46. The plant of embodiment 45, wherein said fungus is at least one of *Colletotrichum graminocola* and *Fusarium graminearum*.

47. The method of embodiment 35, wherein said plant is planted in an area of cultivation, wherein said area of cultivation comprises said plant pathogen, or wherein environmental conditions of said area of cultivation are conducive to the growth of said plant pathogen.

48. The method of embodiment 35, wherein providing the polypeptide comprises introducing into said plant a heterologous polynucleotide comprising a nucleotide sequence selected from the group consisting of:
   (a) the nucleotide sequence set forth in SEQ ID NO: 5, 7, 9, or 11;
   (b) a nucleotide sequence encoding an amino acid sequence comprising SEQ ID NO: 6, 8, 10, or 12;
   (c) a nucleotide sequence having at least 90% sequence identity to SEQ ID NO: 5, 7, 9, or 11, wherein said polynucleotide encodes a polypeptide having antipathogenic activity; and
   (d) a nucleotide sequence encoding an amino acid sequence having at least 85% sequence identity to SEQ ID NO: 6, 8, 10, or 12, wherein said polynucleotide encodes a polypeptide having antipathogenic activity.

49. The method of embodiment 48, wherein said polynucleotide encodes a polypeptide having an amino acid sequence having at least 85% sequence identity to SEQ ID NO: 6, 8, 10, or 12, wherein said polynucleotide encodes a polypeptide having antipathogenic activity, and wherein said amino acid sequence has at least one of the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

50. The method of embodiment 48, wherein said polynucleotide encodes a polypeptide having antifungal activity.

51. The method of embodiment 50, wherein said polypeptide has improved antifungal activity when compared to a polypeptide comprising the amino acid sequence set forth in SEQ ID NO: 2 or 4.

52. The method of embodiment 50, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

53. The method of any one of embodiments 48-52, wherein said polynucleotide is stably integrated into the genome of the plant.

54. The method of any one of embodiments 48-52, wherein said heterologous polynucleotide is operably linked to a promoter active in said plant.

55. The method of embodiment 54, wherein said promoter is a tissue-preferred promoter.

56. The method of embodiment 55, wherein said tissue-preferred promoter is selected from the group consisting of a leaf-preferred promoter, a root-preferred promoter, a seed-preferred promoter, a stalk-preferred promoter, and a vascular tissue-preferred promoter.

57. The method of embodiment 54, wherein said promoter is a pathogen-inducible promoter.

58. An antipathogenic composition comprising at least one polypeptide according to any one of embodiments 1-5.

59. The composition of embodiment 58 further comprising a carrier.

60. A method for protecting a plant from a plant pathogen comprising applying the composition according to embodiment 58 to the environment of a plant pathogen.

61. The method of embodiment 60, wherein said composition is applied by a procedure selected from the group consisting of spraying, dusting, broadcasting, and seed coating.

62. The method of embodiment 60, wherein said plant pathogen is a fungus.

63. The method of embodiment 62, wherein said fungus is at least one of *Colletotrichum graminocola* and *Fusarium graminearum*.

64. A microorganism comprising at least one heterologous polynucleotide operably linked to a promoter that drives expression in the microorganism, wherein said polynucleotide comprises a nucleotide sequence selected from the group consisting of:
  (a) the nucleotide sequence set forth in SEQ ID NO: 5, 7, 9, or 11;
  (b) a nucleotide sequence encoding an amino acid sequence comprising SEQ ID NO: 6, 8, 10, or 12;
  (c) a nucleotide sequence having at least 90% sequence identity to SEQ ID NO: 5, 7, 9, or 11, wherein said polynucleotide encodes a polypeptide having antipathogenic activity; and
  (d) a nucleotide sequence encoding an amino acid sequence having at least 85% sequence identity to SEQ ID NO: 6, 8, 10, or 12, wherein said polynucleotide encodes a polypeptide having antipathogenic activity.

65. The microorganism of embodiment 64, wherein said polynucleotide encodes a polypeptide having an amino acid sequence having at least 85% sequence identity to SEQ ID NO: 4, 6, 8, or 10, wherein said polynucleotide encodes a polypeptide having antipathogenic activity, and wherein said amino acid sequence has at least one of the amino acid residues selected from the group consisting of:
  (a) the arginine (Arg) residue at the position corresponding to residue 1 of SEQ ID NO: 6, 8, 10, or 12;
  (b) the serine (Ser) residue at the position corresponding to residue 16 of SEQ ID NO: 6, 8, 10, or 12;
  (c) the arginine (Arg) residue at the position corresponding to residue 25 of SEQ ID NO: 6, 8, 10, or 12;
  (d) the serine (Ser) residue at the position corresponding to residue 36 of SEQ ID NO: 6, 8, 10, or 12; and
  (e) the serine (Ser) residue at the position corresponding to residue 42 of SEQ ID NO: 6, 8, 10, or 12.

66. The microorganism of embodiment 64, wherein said polynucleotide encodes a polypeptide having antifungal activity.

67. The microorganism of embodiment 66, wherein said polypeptide has improved antifungal activity when compared to a polypeptide comprising the amino acid sequence set forth in SEQ ID NO: 2 or 4.

68. The microorganism of embodiment 66, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

69. An antipathogenic composition comprising at least one microorganism according to any one of embodiments 64-68.

70. The composition of embodiment 69 further comprising a carrier.

71. A method for protecting a plant from a pathogen comprising applying the composition according to embodiment 69 to the environment of a plant pathogen.

72. The method of embodiment 71, wherein said composition is applied by a procedure selected from the group consisting of spraying, dusting, broadcasting, and seed coating.

73. The method of embodiment 71, wherein said plant pathogen is a fungus.

74. The method of embodiment 73, wherein said fungus is at least one of *Colletotrichum graminocola* and *Fusarium graminearum*.

75. A method for controlling a pathogen in an area of cultivation, said method comprising:
  a) evaluating environmental conditions in an area of cultivation for the presence of a pathogen or conditions conducive to the growth of a pathogen;
  b) selecting an effective amount of an antipathogenic composition, wherein the antipathogenic composition is the composition according to embodiment 58 or embodiment 69; and
  c) applying said antipathogenic composition to a crop, crop part, seed, or an area of cultivation of said crop.

76. A method for controlling a pathogen in an area of cultivation, said method comprising:
  a) evaluating environmental conditions in an area of cultivation for the presence of a pathogen or conditions conducive to the growth of a pathogen; and
  b) planting the area with crop seeds or plants comprising a heterologous polynucleotide operably linked to a promoter that drives expression in the plant, wherein said heterologous polynucleotide comprises a nucleotide sequence selected from the group consisting of:
    (i) the nucleotide sequence set forth in SEQ ID NO: 5, 7, 9, or 11;
    (ii) a nucleotide sequence encoding an amino acid sequence comprising SEQ ID NO: 6, 8, 10, or 12;
    (iii) a nucleotide sequence having at least 90% sequence identity to SEQ ID NO: 5, 7, 9, or 11, wherein said polynucleotide encodes a polypeptide having antipathogenic activity; and
    (iv) a nucleotide sequence encoding an amino acid sequence having at least 85% sequence identity to SEQ ID NO: 6, 8, 10, or 12, wherein said polynucleotide encodes a polypeptide having antipathogenic activity.

77. The method of embodiment 76, wherein said polynucleotide encodes a polypeptide having an amino acid sequence having at least 85% sequence identity to SEQ ID NO: 6, 8, 10, or 12, wherein said polynucleotide encodes a polypeptide having antipathogenic activity, and wherein said amino acid sequence has at least one of the amino acid residues selected from the group consisting of:
  (a) the arginine (Arg) residue at the position corresponding to residue 1 of SEQ ID NO: 6, 8, 10, or 12;
  (b) the serine (Ser) residue at the position corresponding to residue 16 of SEQ ID NO: 6, 8, 10, or 12;
  (c) the arginine (Arg) residue at the position corresponding to residue 25 of SEQ ID NO: 6, 8, 10, or 12;
  (d) the serine (Ser) residue at the position corresponding to residue 36 of SEQ ID NO: 6, 8, 10, or 12; and
  (e) the serine (Ser) residue at the position corresponding to residue 42 of SEQ ID NO: 6, 8, 10, or 12.

78. The method of embodiment 76, wherein said polynucleotide encodes a polypeptide having antifungal activity.

79. The method of embodiment 78, wherein said polypeptide has improved antifungal activity when compared to a polypeptide comprising the amino acid sequence set forth in SEQ ID NO: 2 or 4.

80. The method of embodiment 78, wherein said polypeptide has improved antifungal activity against at least one of *Colletotrichum graminocola* and *Fusarium graminearum* when compared to a polypeptide comprising the amino acid sequence set forth in SEQ ID NO: 2 or 4.

81. The method of any one of embodiments 75-80, wherein said pathogen is a fungus.

82. The method of embodiment 81, wherein said fungus is at least one of *Colletotrichum graminocola* and *Fusarium graminearum*.

These and other aspects of the invention are disclosed in more detail in the description of the invention given below.

BRIEF DESCRIPTION OF THE FIGURES

FIG. 1 shows a sequence alignment of the presently disclosed *Picramnia pentandra* plant defensin (Pp-PDF1) variant amino acid sequences with the Pp-PDF1 amino acid sequence (SEQ ID NO: 4).

DETAILED DESCRIPTION OF THE INVENTION

Compositions and methods are provided that are directed to inducing pathogen resistance, particularly fungal resistance, in plants. The compositions include novel nucleotide and amino acid sequences for antipathogenic polypeptides. Specifically, isolated polypeptides having the amino acid sequence set forth in SEQ ID NOs: 6, 8, 10, and 12 and variants and fragments thereof are provided. Isolated polynucleotides, and variants and fragments thereof, comprising nucleotide sequences that encode the amino acid sequences shown in SEQ ID NOs: 6, 8, 10, and 12 are further provided.

The novel antipathogenic polypeptides and nucleotide sequences encoding the same were generated through DNA shuffling with known plant defensin sequences, including the *Picramnia pentandra* plant defensin Pp-PDF1. See U.S. Pat. Nos. 6,911,577 and 7,396,980, each of which are herein incorporated by reference in its entirety. Plant defensins include thionins, small cysteine-rich peptides, proteinase inhibitors, amylase inhibitors, and the like. They are called defensin genes after a structural classification of proteins (SCOP) classification system. Defensins play a role in defense, more specifically plant defense against pathogens, and they share similarity in primary and secondary structure with insect defensins. Defensins of the invention are classified in the superfamily of Scorpion toxin-like proteins and in the Plant Defensin family. While not bound by any mechanism of action, expression of the sequences and related genes around disease induced lesions may control symptom development, as in a hypersensitive response (HR), by controlling the protease mediated cell death mechanism. The compositions may also function directly as antipathogenic proteins by inhibiting proteases produced by pathogens or by binding cell wall components of pathogens. Thirdly, they may also act as amphipathic proteins that perturb membrane function, leading to cellular toxicity of the pathogens. The defensins are generally small cysteine-rich peptides and demonstrate antimicrobial activity.

Plant defensins generally comprise about 45-54 amino acids with four disulfide bridges (Broekaert et al. (1995) *Plant Physiol.* (*Bethesda*) 108:1353-1358). The defensins of the invention inhibit the growth of a broad range of pathogens, including but not limited to fungi, nematodes, bacteria, insects, and viruses at micromolar concentrations. Defensins inhibit pathogen damage through a variety of mechanisms including, but not limited to, alteration of membrane ion permeability and induction of hyphal branching in fungal targets (Garcia-Olmeda et al. (1998) *Biopolymers, Peptide Science* 47:479-491, herein incorporated by reference).

The previously disclosed plant defensins (see U.S. Pat. Nos. 6,911,577 and 7,396,980) were classified into 85 groups based on sequence homology and were referred to as "CS" followed by a three-digit number. The Pp-PDF1 polypeptide used in the DNA shuffling analysis that yielded the presently disclosed Pp-PDF1 variants belongs to Group 18 and is also referred to as CS164. The nucleotide and amino acid sequences for the full-length Pp-PDF1 polypeptide is set forth in SEQ ID NO: 1 and 2, respectively, whereas the nucleotide and amino acid sequences for the mature Pp-PDF1 polypeptide is set forth in SEQ ID NO: 3 and 4, respectively. The Pp-PDF1 polypeptide and presently disclosed variants thereof exhibit antifungal activity against at least the fungi *Fusarium graminearum* (FGR), *Colletotrichum graminicola* (CGR), *Fusarium verticillioides* (FVE) and *Diplodia maydis* (DMA).

Table 1 sets forth IC50 data for Pp-PDF1 and the shuffled variants.

TABLE 1

| AFP | IC50 (ppm) | | | | | | | |
|---|---|---|---|---|---|---|---|---|
| | Low Salt | | | | High Salt | | | |
| | Cgr | Fgr | Fve | Dma | Cgr | Fgr | Fve | Dma |
| Pp-PDF1 (SEQ ID NO: 4) | 3 | 2 | 2 | 7.5 | 15 | 5 | 50 | 50 |
| Pp-PDF1-1C-7A4 (SEQ ID NO: 6) | 0.1 | 4.7 | | | 5 | 20 | >200 | 50 |
| Pp-PDF1-1C-7C4 (SEQ ID NO: 8) | 0.14 | 4.7 | | | 3 | 20 | >200 | 25 |
| Pp-PDF1-1C-6D3 (SEQ ID NO: 23) | 0.6 | 4.5 | | | 12 | | | |
| Pp-PDF1-1F-1C5 (SEQ ID NO: 25) | | | | | 10 | 1.5 | >200 | 50 |
| PP-PDF1-1F-12H3 (SEQ ID NO: 27) | | | | | 10 | 3 | >200 | 200 |

TABLE 1-continued

| | IC50 (ppm) | | | | | | | |
|---|---|---|---|---|---|---|---|---|
| | Low Salt | | | | High Salt | | | |
| AFP | Cgr | Fgr | Fve | Dma | Cgr | Fgr | Fve | Dma |
| PP-PDF1-1F-7H6 (SEQ ID NO: 29) | | | | | 10 | 3 | >200 | 200 |
| Pp-PDF1-2CA-1A6 (SEQ ID NO: 31) | | | | | 1 | | | |
| Pp-PDF1-2CE-4A7 (SEQ ID NO: 33) | | | | | 0.8 | 5.6 | 200 | 25 |
| Pp-PDF1-2CA-1H4 (SEQ ID NO: 35) | | | | | 1 | | | |
| Pp-PDF1 2CA 5H4 (SEQ ID NO: 37) | | | | | 1 | | | |
| PP-PDF1-2CF-2D8 (SEQ ID NO: 39) | 0.3 | 15 | 30 | 15 | 0.6 | 100 | 200 | 50 |
| PP-PDF1-2CF-10F3 (SEQ ID NO: 41) | 1.5 | 15 | 30 | 15 | 0.6 | 100 | 200 | 25 |
| PP-PDF1-2CE-4B11 (SEQ ID NO: 12) | | | | | 0.8 | >200 | >200 | 12.5 |
| Pp-PDF1-3CA-1A2 (SEQ ID NO: 43) | 3 | 15 | 30 | 15 | 0.6 | ~100 | 200 | 50 |
| Pp-PDF1-3CA-1A7 (SEQ ID NO: 45) | 0.8 | 15 | 30 | 10 | 0.6 | ~100 | 200 | 25 |
| Pp-PDF1-3CA-1B2 (SEQ ID NO: 47) | 2 | 15 | 30 | 15 | 0.8 | ~100 | 200 | 50 |
| Pp-PDF1-3CA-1 E6 (SEQ ID NO: 49) | | | | | 0.6 | ~100 | | |
| Pp-PDF1-3CA-2D3 (SEQ ID NO: 51) | 0.3 | 15 | 30 | 6 | 0.8 | ~100 | 200 | 25 |
| Pp-PDF1-4CB-6E6 (SEQ ID NO: 53) | 0.25 | | | | 0.25 | 150 | >200 | 100 |
| Pp-PDF1-4CB-6E9 (SEQ ID NO: 55) | 0.4 | | | | 0.25 | 150 | >200 | 100 |
| Pp-PDF1-4CB-12G9 (SEQ ID NO: 57) | 0.25 | | | | 0.25 | 50 | >200 | 25 |

The presently disclosed Pp-PDF1 polypeptide variants (SEQ ID NOs: 6, 8, 10 and 12) identified through DNA shuffling exhibit improved activity against at least one pathogenic target when compared to the parent polypeptide (e.g., SEQ ID NO: 2 or 4). In some embodiments, the presently disclosed Pp-PDF1 variants exhibit improved antifungal activity against at least one of F. graminearum and Colletotrichum graminicola. The variant Pp-PDF1 nucleotide sequences are set forth in SEQ ID NOs: 5, 7, 9 and 11.

Plants, plant cells, seeds, and microorganisms comprising a polynucleotide that encodes a presently disclosed antipathogenic polypeptide of the invention are also disclosed herein. Antipathogenic compositions comprising an isolated antipathogenic, particularly an antifungal, polypeptide or a microorganism that expresses a presently disclosed polypeptide in combination with a carrier are further provided. The compositions find use in generating pathogen-resistant plants and in protecting plants from pathogens, particularly fungal pathogens.

The polynucleotides and polypeptides of the present invention find use in methods for inducing pathogen resistance in a plant. Accordingly, the compositions and methods disclosed herein are useful in protecting plants against plant pathogens. By "plant pathogen" is intended any organism that can cause harm to a plant by inhibiting or slowing the growth of a plant, by damaging the tissues of a plant, by weakening the immune system of a plant, reducing the resistance of a plant to abiotic stresses, and/or by causing the premature death of the plant, etc. Plant pathogens include fungi, viruses, bacteria, nematodes and the like.

"Pathogen resistance" or "disease resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss.

"Antipathogenic compositions" or "antipathogenic polypeptides" is intended to mean that the compositions of the invention have antipathogenic activity and thus are capable of suppressing, controlling, and/or killing the invading pathogenic organism. An antipathogenic polypeptide or composition of the invention will reduce the disease symptoms resulting from pathogen challenge by at least about 2%, including but not limited to, about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater. In particular embodiments, the disease symptoms resulting from pathogen challenge are reduced by an antipathogenic polypeptide or composition of the invention by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In particular embodiments, the antipathogenic activity exhibited by the polypeptides of the invention is antifungal activity. As used herein, "antifungal activity" refers to the ability to suppress, control, and/or kill the invading fungal pathogen. Likewise, "fungal resistance" refers to enhanced tolerance to a fungal pathogen when compared to that of an untreated or wild type plant. Resistance may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens may both constitute antifungal activity or improved fungal resistance. Likewise, a polypeptide having "improved antipathogenic activity" or "improved antifungal activity" can refer to a polypeptide exhibiting an increase in activity against a single pathogen or fungus or activity against a wider spectrum of pathogens or fungi as compared to a reference polypeptide.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface or environment shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antifungal activity are also well known in the art. See, for example, Duvick et al. (1992) *J. Biol. Chem.* 267: 18814-18820; Lacadena et al. (1995) *Arch. Biochem. Biophys.* 324:273-281; Xu et al. (1997) *Plant Mol. Biol.* 34: 949-959; Lee et al. (1999) *Biochem. Biophys. Res. Comm.* 263:646-651; Vila et al. (2001) *Mol. Plant. Microbe Interact.* 14:1327-1331; Moreno et al. (2003) *Phytpathol.* 93:1344-1353; Kaiserer et al. (2003) *Arch. Microbiol.* 180:204-210; and U.S. Pat. No. 6,015,941; each of which are herein incorporated by reference.

In some embodiments, the presently disclosed antipathogenic polypeptides or variants or fragments thereof display improved antipathogenic, particularly antifungal, activity when compared to the parent polypeptide from which it was derived through DNA shuffling technology (e.g., SEQ ID NO: 2 or 4). In certain embodiments, the presently disclosed antipathogenic polypeptide exhibits a 2-fold to 100-fold greater antipathogenic activity against at least one susceptible pathogen than the parent polypeptide, including but not limited to, about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 50-fold, 60-fold, 70-fold, 80-fold, 90-fold, and 100-fold. The antipathogenic activity against a particular pathogen can be measured using any method known in the art, including but not limited to the in vitro assays described above and the antifungal plate assay described in Example 2. The antifungal plate assay can be performed under either low or high salt conditions. Low Salt is ⅛× concentration of liquid media (potato dextrose broth for *Diplodia maydis, Fusarium graminearum*, and *Fusarium verticillioides*, Czapek-Dox broth for *Colletotrichum graminocola*) plus 0.25 mM calcium chloride, 12.5 mM potassium chloride. High salt is ½× liquid media, as described above, plus 1 mM calcium chloride, 50 mM potassium chloride.

In certain embodiments, a presently disclosed antipathogenic polypeptide or variant or fragment thereof exhibits greater antifungal activity against at least one of *Colletotrichum graminocola* and *Fusarium graminearum*. In particular embodiments, the antipathogenic polypeptide displays about a 15-fold increase in antifungal activity against the fungus *Colletotrichum graminocola* in an in vitro antifungal plate assay (such as that described in Example 2) performed under high salt conditions or about a 45-fold improved activity against *C. graminicola* in a similar assay performed under low salt conditions when compared to the polypeptide set forth in SEQ ID NO: 2 or 4. In other embodiments, the antipathogenic polypeptide displays about a 3-fold increase in antifungal activity against the fungus *Fusarium graminearum* in an in vitro antifungal plate assay performed under high salt conditions when compared to the polypeptide set forth in SEQ ID NO: 2 or 4.

The compositions disclosed herein comprise isolated polynucleotides that encode antipathogenic polypeptides, expression cassettes comprising the presently disclosed antipathogenic polynucleotides, and isolated antipathogenic polypeptides. Antipathogenic compositions comprising a presently disclosed polypeptide in combination with a carrier are also provided. The invention further discloses plants and microorganisms comprising polynucleotides that encode antipathogenic proteins.

As used herein, "polynucleotide" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The presently disclosed polynucleotides also encompass all forms of sequences including, but not limited to, single-stranded forms, double-stranded forms, hairpins, stem-and-loop structures, and the like.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a polynucleotide disclosed herein, or by the use of standard molecular biology or biochemical techniques. For example, a truncated protein of the invention can be produced by expression of a recombinant polynucleotide of the invention in an appropriate host cell, or alternatively by a combination of ex vivo procedures, such as protease digestion and purification.

As used herein, the terms "encoding" or "encoded" when used in the context of a specified polynucleotide mean that the polynucleotide comprises the requisite information to direct translation of the nucleotide sequence into a specified protein. The information by which a protein is encoded is specified by the use of codons. A polynucleotide encoding a protein may comprise non-translated sequences (e.g., introns) within translated regions of the polynucleotide or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment (or the naturally occurring environment of the parent defensin polynucleotide or protein). Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the parent defensin is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the parent defensin polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the presently disclosed antipathogenic protein or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain the biological activity of a presently disclosed antipathogenic protein and hence have antipathogenic activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, and up to the full-length polynucleotide encoding the presently disclosed proteins.

A fragment of a polynucleotide that encodes a biologically active portion of a presently disclosed antipathogenic protein will encode at least 15, 25, 30, or 50 contiguous amino acids, or up to the total number of amino acids present in a full-length antipathogenic protein of the invention (for example, 50 amino acids for SEQ ID NOs: 6, 8, 10, and 12). Fragments of a polynucleotide that are useful as hybridization probes or PCR primers generally need not encode a biologically active portion of an antipathogenic protein.

Thus, a fragment of a presently disclosed polynucleotide may encode a biologically active portion of an antipathogenic polypeptide, or it may be a fragment that can be used as a hybridization probe or PCR primer using methods disclosed below. A biologically active portion of an antipathogenic polypeptide can be prepared by isolating a portion of one of the polynucleotides of the invention, expressing the encoded portion of the antipathogenic protein (e.g., by recombinant expression in vitro), and assessing the activity of the encoded portion of the antipathogenic protein. Polynucleotides that are fragments of a nucleotide sequence of the invention comprise at least 16, 20, 50, 75, 100, or 150 contiguous nucleotides, or up to the number of nucleotides present in a full-length polynucleotide disclosed herein (for example, 150 nucleotides for SEQ ID NOs: 5, 7, 9, or 11).

"Variants" is intended to mean substantially similar sequences. For polynucleotides, a variant comprises a deletion and/or addition of one or more nucleotides at one or more internal sites within an antipathogenic polynucleotide disclosed herein and/or a substitution of one or more nucleotides at one or more sites in a presently disclosed antipathogenic polynucleotide.

For polynucleotides, conservative variants include those sequences that, because of the degeneracy of the genetic code, encode the amino acid sequence of one of the antipathogenic polypeptides of the invention. Variant polynucleotides can be synthetically derived polynucleotides, such as those generated, for example, by using site-directed mutagenesis but which still encode an antipathogenic protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 6, 8, 10, or 12 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from an antipathogenic protein disclosed herein by deletion or addition of one or more amino acids at one or more internal sites in the presently disclosed antipathogenic protein and/or substitution of one or more amino acids at one or more sites in the antipathogenic protein. Variant proteins encompassed by the present invention are biologically active, that is they continue to possess the desired biological activity of a presently disclosed antipathogenic protein, that is, antipathogenic activity as described herein. Such variants may result from, for example, human manipulation. Biologically active variants of a presently disclosed antipathogenic protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the presently disclosed antipathogenic protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

In some embodiments, variants of the polypeptides of the invention retain the amino acid residues that differ from the parent polypeptide (e.g., SEQ ID NO: 4) that can contribute to the enhanced antipathogenic activity of the presently disclosed polypeptides (those amino acid residues can be determined by consulting the alignment shown in FIG. 1). For example, variants of SEQ ID NO: 6, 8, 10, or 12 can comprise at least one of the following amino acid residues: the arginine (Arg) residue at the position corresponding to residue 1 of SEQ ID NO: 6, 8, 10, or 12; the serine (Ser) residue at the position corresponding to residue 16 of SEQ ID NO: 6, 8, 10, or 12; the arginine (Arg) residue at the position corresponding to residue 25 of SEQ ID NO: 6, 8, 10, or 12; the serine (Ser) residue at the position corresponding to residue 36 of SEQ ID NO: 6, 8, 10, or 12; and the serine (Ser) residue at the position corresponding to residue 42 of SEQ ID NO: 6, 8, 10, or 12. In certain embodiments, the variants of SEQ ID NO: 6, 8, 10, or 12 can comprise an asparagine (Asn) or histidine (His) residue at the position corresponding to residue 22 of SEQ ID NO: 6, 8, 10, or 12. In particular embodiments, the variants of SEQ ID NO: 6, 8, 10, or 12 can comprise a lysine (Lys) or threonine (Thr) residue at the position corresponding to residue 47 of SEQ ID NO: 6, 8, 10, or 12. In particular, the serine residues at positions 36 and 42 are associated with improved activity, particularly improved CGR activity.

The proteins of the invention may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure antipathogenic activity such as antifungal plate assays. See, for example, Duvick et al. (1992) *J. Biol. Chem.* 267:18841-18820, herein incorporated by reference.

Variant polynucleotides and proteins also encompass sequences and proteins derived from a mutagenic and recombinogenic procedure such as DNA shuffling. With such a procedure, one or more different antipathogenic protein coding sequences can be manipulated to create a new antipathogenic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the presently disclosed antipathogenic polynucleotides and other known antipathogenic genes, such as, for example, defensin genes, to obtain a new gene coding for a protein with an improved property of interest, such as increased antipathogenic activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants, more particularly other fungi. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Thus, isolated polynucleotides that encode for an antipathogenic protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A*

*Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among antipathogenic polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In particular aspects, methods for inducing pathogen resistance in a plant comprise introducing into a plant at least one polynucleotide, wherein the polynucleotide comprises a nucleotide sequence encoding an antipathogenic polypeptide of the invention. The polynucleotide is operably linked to a promoter that drives expression in the plant. The plant expresses the antipathogenic polypeptide, thereby exposing the pathogen to the polypeptide at the site of pathogen attack. In particular embodiments, the polypeptides have antifungal activity, and the pathogen is a fungus, such as, for example, *Fusarium graminearum* or *Colletotrichum graminocola*. Expression of an antipathogenic polypeptide of the invention may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters. Moreover, the polypeptides of the invention may also be targeted to specific subcellular locations within a plant cell or, alternatively, secreted from the cell, as described herein below.

Just as expression of an antipathogenic polypeptide of the invention may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location. In particular embodiments, a nucleotide sequence encoding a barley alpha-amylase (BAA) signal peptide is joined in frame with a polynucleotide of the invention. The nucleotide sequence encoding the BAA signal peptide and the amino acid sequence for the BAA signal peptide are set forth in SEQ ID NO: 13 and SEQ ID NO: 14, respectively.

Other pathogens may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art and include, for example, KDEL (SEQ ID NO: 15), SEKDEL (SEQ ID NO: 16), HDEL (SEQ ID NO: 17), and HDEF (SEQ ID NO: 18). See, for example, Denecke et al. (1992). *EMBO J.* 11:2345-2355; Wandelt et al. (1992) *Plant J.* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481. Chloroplast targeting sequences that encode such transit peptides are also known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.*

263:14996-14999). A person skilled in the art could also envision generating transgenic plants in which the chloroplasts have been transformed to overexpress a gene for an antipathogenic peptide. See, for example, Daniell (1999) *Nature Biotech* 17:855-856; and U.S. Pat. No. 6,338,168.

One could also envision localizing the antipathogenic polypeptide in other cellular compartments by addition of suitable targeting information. (Raikhel and Chrispeels, supra). A useful site available on the world wide web that provides information and references regarding recognition of the various targeting sequences can be found at: psort.nibb.ac.jp/mit. Other references regarding the state of the art of protein targeting include Silva-Filho (2003) *Curr. Opin. Plant Biol.* 6:589-595; Nicchitta (2002) *Curr. Opin. Cell Biol.* 14:412-416; Bruce (2001) *Biochim Biophys Acta* 1541: 2-21; Hadlington & Denecke (2000) *Curr. Opin. Plant Biol.* 3: 461-468; Emanuelsson et al. (2000) *J Mol. Biol.* 300: 1005-1016; Emanuelsson & von Heijne (2001) *Biochim Biophys Acta* 1541: 114-119, herein incorporated by reference.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding. In some embodiments, the antipathogenic polypeptides of the invention are expressed as fusion proteins, wherein the propeptide segments (optionally preceded by a signal peptide) of the Pp-PDF1 protein or another antipathogenic polypeptide (e.g., another defensin) is fused to the amino terminal end of the polypeptide of the invention. The nucleotide and amino acid sequence for the Pp-PDF1 propeptide is set forth in SEQ ID NO: 19 and 20, respectively.

The polynucleotides of the present invention can be expressed in a host cell, such as a bacterial, fungal, yeast, insect, mammalian, or preferably plant cells. By "host cell" is meant a cell which comprises a heterologous polynucleotide of the invention. Host cells may be prokaryotic cells, such as *E. coli*, or eukaryotic cells, such as yeast, insect, amphibian, or mammalian cells. In some embodiments, host cells are monocotyledonous or dicotyledonous plant cells. In particular embodiments, the monocotyledonous host cell is a maize host cell.

The antipathogenic polynucleotides of the invention can be provided in expression cassettes for expression in an organism of interest. The expression cassettes of the invention find use in generating transformed plants, plant cells, and microorganisms and in practicing the methods for inducing pathogen resistance disclosed herein. The cassette will include 5' and 3' regulatory sequences operably linked to an antipathogenic polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions.

The expression cassette will include in the 5'-3' direction of transcription, a transcriptional and translational initiation region (i.e., a promoter), a polynucleotide of the invention, and a transcriptional and translational termination region (i.e., termination region) functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato proteinase inhibitor II gene (PinII) terminator is used. See, for example, Keil et al. (1986) *Nucl. Acids Res.* 14:5641-

5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome. A wide range of plant promoters are discussed in the review of Potenza et al. (2004) *In Vitro Cell Dev Biol—Plant* 40:1-22, herein incorporated by reference. For example, the nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200) and the inducible maize promoters described in U.S. Pat. No. 6,429,362 (e.g., Zm-PR1-81 and Zm-PR1-83 promoters), all of which are herein incorporated by reference in their entirety. The promoters described in U.S. Pat. No. 6,720,480, such as the Zm-BB11 promoter, may also be used in the practice of the invention.

Additionally, as pathogens find entry into plants through wounds or insect damage, a wound-inducible promoter, which includes a pathogen-inducible promoter, may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.*

14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the antipathogenic polypeptides of the invention within a particular plant tissue. For example, a tissue-preferred promoter may be used to express an antipathogenic polypeptide in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, but are not limited to, the *Prunus serotina* prunasin hydrolase gene promoter (see, e.g., International Publication No. WO 03/006651), and also those found in U.S. Pat. No. 6,921,815.

Stalk-preferred promoters may be used to drive expression of an antipathogenic polypeptide of the invention. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735. In certain embodiments of the invention, the Zm-419 promoter is used for tissue preferred-expression in maize stalk tissue. See, for example, International Publication No. WO 2007/050509 and U.S. Pat. No. 7,538,261.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553;

Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235 and Mosbach et al. (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Synthesis of heterologous nucleotide sequences in yeast is well known. Sherman, F., et al. (1982) *Methods in Yeast Genetics*, Cold Spring Harbor Laboratory is a well recognized work describing the various methods available to produce proteins in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like, as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al. (1983) *J. Virol.* 45:773-781). Additionally, gene sequences to control replication in the host cell may be incorporated into the vector such as those found in bovine papilloma virus type-vectors. Saveria-Campo, M., (1985) Bovine Papilloma Virus DNA a Eukaryotic Cloning Vector in *DNA Cloning Vol. II a Practical Approach*, D. M. Glover, Ed., IRL Press, Arlington, Va. pp. 213-238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J. (1997) *Biochemical Methods in Cell Culture and Virology*, Dowden, Hutchinson and Ross, Inc.

In certain embodiments, the polynucleotides of the present invention can be stacked with any combination of polynucleotide sequences of interest in order to create plants with a desired phenotype. For example, the polynucleotides of the present invention may be stacked with other antipathogenic genes and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)); the disclosures of which are herein incorporated by reference.

The polynucleotides of the present invention can also be stacked with traits desirable for insect, disease, or herbicide resistance (e.g., *Bacillus thuringiensis* toxic proteins (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089), including but not limited to, other plant defensin genes (U.S. Pat. Nos. 6,911,577 and 7,396,980); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the antipathogenic sequences of the invention can be provided to a plant using a variety of transient transformation methods. Such transient transformation methods include, but are not limited to, the introduction of the antipathogenic protein or variants and fragments thereof directly into the plant or the introduction of antipathogenic protein transcript into the plant. Such methods include, for example, microinjection or particle bombardment. See, for example, Crossway et al. (1986) *Mol Gen. Genet.* 202: 179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the antipathogenic polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations, the heterozygous condition gives way to homogeneous lines as a result of self-pollination and selection. Typically in the pedigree method of breeding, five or more successive filial generations of selfing and selection is practiced: F1→F2; F2→F3; F3→F4; F4→$F_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased pathogen resistance), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and toperos sing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used to induce pathogen resistance or protect from pathogen attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The compositions of the invention find further use in methods directed to protecting a plant from a pathogen. "Protecting a plant from a pathogen" is intended to mean killing the pathogen or preventing or limiting disease formation on a plant. In some embodiments, an antipathogenic composition comprising an antipathogenic polypeptide and a carrier is applied directly to the environment of a plant pathogen, such as, for example, on a plant or in the soil or other growth medium surrounding the roots of the plant, in order to protect the plant from pathogen attack. Microorganisms comprising a polynucleotide encoding an antipathogenic protein of the invention and methods of using them to protect a plant from a pathogen are further provided. In some embodiments, the transformed microorganism is applied directly to a plant or to the soil in which a plant grows.

Antipathogenic compositions, particularly antifungal compositions, are also encompassed by the present invention. Antipathogenic compositions may comprise antipathogenic polypeptides or microorganisms comprising a heterologous polynucleotide that encodes an antipathogenic polypeptide.

The antipathogenic compositions of the invention may be applied to the environment of a plant pathogen, as described herein below, thereby protecting a plant from pathogen attack. Moreover, an antipathogenic composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The antipathogenic compositions find further use in the decontamination of plant pathogens during the processing of grain for animal or human food consumption; during the processing of feedstuffs, and during the processing of plant material for silage. In this embodiment, the defensins of the invention are presented to grain, plant material for silage, or a contaminated food crop, or during an appropriate stage of the processing procedure, in amounts effective for antimicrobial activity.

A polynucleotide encoding an antipathogenic, particularly antifungal, polypeptide of the invention may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the antipathogenic protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Other illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Polynucleotides encoding the antipathogenic proteins of the invention can be introduced into microorganisms that multiply on plants (epiphytes) to deliver antipathogenic proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Polynucleotides encoding the antipathogenic polypeptides of the invention can be introduced into a root-colonizing *Bacillus cereus* by standard methods known in the art.

Polynucleotides encoding antipathogenic proteins can be introduced, for example, into the root-colonizing *Bacillus* by means of electrotransformation. Specifically, polynucleotides encoding the antipathogenic proteins can be cloned into a shuttle vector, for example, pHT3101 (Lerecius et al. (1989) *FEMS Microbiol. Letts.* 60: 211-218. The shuttle vector pHT3101 containing the coding sequence for the particular antipathogenic protein can, for example, be transformed into the root-colonizing *Bacillus* by means of electroporation (Lerecius et al. (1989) *FEMS Microbiol. Letts.* 60: 211-218).

Methods are provided for protecting a plant from a pathogen comprising applying an effective amount of an antipathogenic protein or composition of the invention to the environment of the pathogen. "Effective amount" is intended to mean an amount of a protein or composition sufficient to control a pathogen. The antipathogenic proteins and compositions can be applied to the environment of the pathogen by methods known to those of ordinary skill in the art.

Prior to the application of an antipathogenic composition of the invention to an area of cultivation, the environment can be evaluated to determine if the pathogen of interest is present or if conditions are conducive to pathogen growth or infestation. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Evaluation of the environment can aid in determining the effective amount of the antipathogenic protein or composition of the invention needed to control a pathogen within an area of cultivation.

Environmental conditions that can be evaluated include, but are not limited to, ground and surface water pollution concerns, intended use of the crop, crop tolerance, soil residuals, weeds present in area of cultivation, humidity, soil texture, pH of soil, amount of organic matter in soil, water content of soil, application equipment, and tillage practices. Following the evaluation of the environmental conditions, an effective amount of an antipathogenic composition of the invention can be applied to the crop, crop part, seed of the crop or area of cultivation.

The antipathogenic compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antipathogenic proteins, more particularly antifungal proteins, of the present invention include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antipathogenic compositions of the present invention can be in a suitable form for direct application or as a concentrate of primary composition that requires dilution with a suitable quantity of water or other diluent before application. The concentration of the antipathogenic polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

In a further embodiment, the compositions, as well as the transformed microorganisms and antipathogenic proteins, of the invention can be treated prior to formulation to prolong the antipathogenic, particularly antifungal, activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The antipathogenic compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antipathogenic protein and/or transformed microorganisms of the invention may be mixed with grain to protect the grain during storage. It is generally important to obtain good control of pathogens in the early stages of plant growth, as this is the time when the plant can be most severely damaged. In one embodiment of the invention, the composition is applied directly to the soil, at a time of planting, in granular form of a composition of a carrier and antipathogenic polypeptides or transformed microorganisms of the invention. Another embodiment is a granular form of a composition comprising an agrochemical such as, for example, a herbicide, an insecticide, a fertilizer, an inert carrier, and antipathogenic polypeptides or transformed microorganisms of the invention.

Compositions of the invention find use in protecting plants, seeds, and plant products in a variety of ways. For example, the compositions can be used in a method that involves placing an effective amount of the antipathogenic, more particularly, antifungal, composition in the environment of the pathogen by a procedure selected from the group consisting of spraying, dusting, broadcasting, or seed coating.

The time at which an antipathogenic composition is applied to an area of interest (and any plants therein) may be important in optimizing pathogen control. The time at which an antipathogenic composition is applied may be determined with reference to the size of plants and/or the stage of growth and/or development of plants in the area of interest. The stages of growth and/or development of plants are known in the art. For example, soybean plants normally progress through vegetative growth stages known as VE (emergence), VC (cotyledon), V1 (unifoliate), and V2 to VN. Soybeans then switch to the reproductive growth phase in response to photoperiod cues; reproductive stages include R1 (beginning bloom), R2 (full bloom), R3 (beginning pod), R4 (full pod), R5 (beginning seed), R6 (full seed), R7 (beginning maturity), and R8 (full maturity). Corn plants normally progress through the following vegetative stages VE (emergence); V1 (first leaf); V2 (second leaf); V3 (third leaf); V(n) (Nth/leaf); and VT (tasseling). Progression of maize through the reproductive phase is as follows: R1 (silking); R2 (blistering); R3 (milk); R4 (dough); R5 (dent); and R6 (physiological maturity). Cotton plants normally progress through VE (emergence), VC (cotyledon), V1 (first true leaf), and V2 to VN. Then, reproductive stages beginning around V14 include R1 (beginning bloom), R2 (full bloom), R3 (beginning boll), R4 (cutout, boll development), R5 (beginning maturity, first opened boll), R6 (maturity, 50% opened boll), and R7 (full maturity, 80-90% open bolls). Thus, for example, the time at which an antipathogenic composition or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

One of skill in the art will appreciate that the compositions and methods disclosed herein can be used with other compositions and methods available in the art for protecting plants from insect and pathogen attack. For example, methods of the invention can comprise the use of one or more herbicides, insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. General references for these agricultural protectants include The Pesticide Manual, 13th Edition, C. D. S. Tomlin, Ed., British Crop Protection Council, Farnham, Surrey, U.K., 2003 and The BioPesticide Manual, 2nd Edition, L. G. Copping, Ed., British Crop Protection Council, Farnham, Surrey, U.K., 2001.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a polynucleotide encoding an antipathogenic polypeptide of the invention may be treated with a seed protective coating comprising a seed treatment compound, such as, for example, captan, carboxin, thiram, methalaxyl, pirimiphos-methyl, and others that are commonly used in seed treatment. Alternatively, a seed of the invention comprises a seed protective coating comprising an antipathogenic, more particularly antifungal, composition of the invention used alone or in combination with one of the seed protective coatings customarily used in seed treatment.

In an embodiment of the invention, the antipathogenic compositions of the invention may be used as a pharmaceutical composition for the treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary cryptococcus, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

In some of these embodiments, the antipathogenic polypeptide is combined with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

In particular, the antipathogenic polypeptides of the invention and pharmaceutical compositions comprising the same may be used to provide treatment for diseases and disorders associated with, but not limited to, the following fungal pathogens: *Histoplasma capsulatum, Candida* spp. (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus* spp., *Rhizomucor* spp., *Cunninghamella* spp., *Apophysomyces* spp., *Saksenaee* spp., *Mucor* spp., and *Absidia* spp. Efficacy of the compositions of the invention as anti-fungal treatments may be determined through anti-fungal assays known to one in the art.

The presently disclosed pharmaceutical compositions may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the polypeptides and pharmaceutical compositions of the invention.

The antipathogenic polypeptides of the invention can be used for any application including coating surfaces to target microbes. In this manner, target microbes include human pathogens or microorganisms. Surfaces that might be coated with the defensins of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The embodiments of the present invention may be effective against a variety of plant pathogens, particularly fungal pathogens, such as, for example, *Colletotrichum graminocola* and *Fusarium graminearum*. Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminocola*, *Diplodia maydis*, *Fusarium graminearum*, and *Fusarium verticillioides*. Specific pathogens for the major crops include: Soybeans: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassicicola*, *Pythium ultimum*, *Peronospora parasitica*, *Fusarium roseum*, *Alternaria alternata*; Alfalfa: *Clavibacter michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium oxysporum*, *Verticillium alboatrum*, *Xanthomonas campestris* p.v. *alfalfae*, *Aphanomyces euteiches*, *Stemphylium herbarum*, *Stemphylium alfalfae*, *Colletotrichum trifolii*, *Leptosphaerulina briosiana*, *Uromyces striatus*, *Sclerotinia trifoliorum*, *Stagonospora meliloti*, *Stemphylium botryosum*, *Leptotrichila medicaginis*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Plasmopora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Colletotrichum graminicola*, *Fusarium moniliforme* var. *subglutinans*, *Erwinia stewartii*, *F. verticillioides*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *C. sublineolum*, *Cercospora sorghi*, *Gloeocercospora sorghi*, *Ascochyta*

*sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include, but are not limited to, parasitic nematodes such as root-knot, cyst, and lesion nematodes, including *Heterodera* and *Globodera* spp.; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode). Additional nematodes include: *Heterodera cajani; Heterodera trifolii; Heterodera oryzae; Globodera tabacum; Meloidogyne incognita; Meloidogyne javonica; Meloidogyne hapla; Meloidogyne arenaria; Meloidogyne naasi; Meloidogyne exigua; Xiphinema index; Xiphinema italiae; Xiphinema americanum; Xiphinema diversicaudatum; Pratylenchus penetrans; Pratylenchus brachyurus; Pratylenchus zeae; Pratylenchus coffeae; Pratylenchus thornei; Pratylenchus scribneri; Pratylenchus vulnus; Pratylenchus curvitatus; Radopholus similis; Radopholus citrophilus; Ditylenchus dipsaci; Helicotylenchus multicintus; Rotylenchulus reniformis; Belonolaimus* spp.; *Paratrichodorus anemones; Trichodorus* spp.; *Primitivus* spp.; *Anguina tritici; Bider avenae; Subanguina radicicola; Tylenchorhynchus* spp.; *Haplolaimus seinhorsti; Tylenchulus semipenetrans; Hemicycliophora arenaria; Belonolaimus langicaudatus; Paratrichodorus xiphinema; Paratrichodorus christiei; Rhadinaphelenchus cocophilus; Paratrichodorus minor; Hoplolaimus galeatus; Hoplolaimus columbus; Criconemella* spp.; *Paratylenchus* spp.; *Nacoabbus aberrans; Aphelenchoides besseyi; Ditylenchus angustus; Hirchmaniella* spp.; *Scutellonema* spp.; *Hemicriconemoides kanayaensis; Tylenchorynchus claytoni*; and *Cacopaurus pestis*.

The presently disclosed antipathogenic polypeptides can display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (*Xylomyges*) *curialis* Grote (citrus cutworm); *Euxoa messoria* Harris (darksided cutworm); *Helicoverpa armigera* Hubner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* J E Smith (fall armyworm); *S. exigua* Hubner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hubner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubdalis* Hubner (European corn borer); *Plodia interpunctella* Hubner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria*

Hubner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leafmining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are those of the order Hemiptera such as, but not limited to, the following families: Adelgidae, Aleyrodidae, Aphididae, Asterolecamidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptacoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tingidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cornitermes cumulans* Kollar, *Cylindrotermes nordenskioeldi* Holmgren and *Pseudacanthotermes militaris* Hagen (sugarcane termite); as well as those in the Rhinotermitidae family including, but not limited to *Heterotermes tenuis* Hagen. Insects of the order Thysanoptera are also of interest, including but not limited to thrips, such as *Stenchaetothrips minutus* van Deventer (sugarcane thrips).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXPERIMENTAL

Example 1

DNA Shuffling

Gene shuffling utilized coding sequence of Pp-PDF1 mature peptide. Limited diversity was introduced from related defensin sequences by spiking of synthetic oligonucleotides into the shuffling (assembly) reactions. The amino acid changes that contributed to improved activity are the serine residues at positions 36 and 42 of the variants with improved CGR activity. See FIG. 1. The round of shuffling in which each variant was identified is indicated in the sequence naming structure. Variants whose names begin Pp-PDF1-1 came from the first shuffling round; Pp-PDF1-2 came from the second shuffling round; Pp-PDF1-3 came from the third shuffling round; Pp-PDF1-4 came from the fourth shuffling round.

After one round of DNA shuffling, a Pp-PDF1 gene variant, Pp-PDF1-1C-7A4 (SEQ ID NO: 6), was isolated. The Pp-PDF1-1C-7A4 variant showed significantly improved in vitro inhibitory activity against the stalk rot-causing fungus Colletotrichum graminicola (CGR; see Example 2). Additional variants were identified after one round of shuffling including Pp-PDF1-1C-7C4 (SEQ ID NO: 8), Pp-PDF1 (C2B5) (SEQ ID NO: 10), Pp-PDF1 (4B11) (SEQ ID NO: 12), Pp-PDF1-1C-6D3 (SEQ ID NO: 23), Pp-PDF1-1F-1C5 (SEQ ID NO: 25), PP-PDF1-1F-12H3 (SEQ ID NO: 27) and PP-PDF1-1F-7H6 (SEQ ID NO: 29). The nucleotide sequences for these Pp-PDF1 variants are set forth in SEQ ID NOs: 5, 7, 9, 11, 21, 22, 24, 26 and 28.

After two rounds of shuffling, Pp-PDF1 gene variants were identified including Pp-PDF1-2CA-1A6 (SEQ ID NO: 31), Pp-PDF1-2CE-4A7 (SEQ ID NO: 33), Pp-PDF1-2CA-1H4 (SEQ ID NO: 35), Pp-PDF1-2CA-5H4 (SEQ ID NO: 37), PP-PDF1-2CF-2D8 (SEQ ID NO: 39), Pp-PDF1-2CF-10F3 (SEQ ID NO: 41) and PP-PDF1-2CE-41G2 (SEQ ID NO: 59). The nucleotide sequences for these Pp-PDF1 variants are set forth in SEQ ID NOs: 30, 32, 34, 36, 38, 40 and 58.

After three rounds of shuffling, Pp-PDF1 gene variants were identified including Pp-PDF1-3CA-1A2 (SEQ ID NO: 43), Pp-PDF1-3CA-1A7 (SEQ ID NO: 45), Pp-PDF1-3CA-1B2 (SEQ ID NO: 47), Pp-PDF1-3CA-1E6 (SEQ ID NO: 49) and Pp-PDF1-3CA-2D3 (SEQ ID NO: 51). The nucleotide sequences for these Pp-PDF1 variants are set forth in SEQ ID NOs: 42, 44, 46, 48 and 50.

After four rounds of shuffling, Pp-PDF1 gene variants were identified including Pp-PDF1-4CB-6E6 (SEQ ID NO: 53), Pp-PDF1-4CB-6E9 (SEQ ID NO: 55) and Pp-PDF1-4CB-12G9 (SEQ ID NO: 57). The nucleotide sequences for these Pp-PDF1 variants are set forth in SEQ ID NOs: 52, 54 and 56.

Example 2

Antifungal Plate Assay

The antifungal activity of the defensin variants against Fusarium graminearum (FGR; isolate 73B ISU) and Colletotrichum graminicola (CGR; isolate Carroll-IA-99) was assessed using a standard plate assay. As indicated above, low Salt is ⅛× concentration of liquid media (potato dextrose broth for Diplodia maydis, Fusarium graminearum, and Fusarium verticillioides, Czapek-Dox broth for Colletotrichum graminocola) plus 0.25 mM calcium chloride, 12.5 mM potassium chloride. High salt is ½× liquid media plus 1 mM calcium chloride, 50 mM potassium chloride.

Preparation of Cultures for Spore Production

Cultures of FVE were prepared using V8 agar plates. FGR, CGR, and DMA cultures were prepared using ½× oatmeal agar. Media recipes are provided below.

Specifically, tubes containing silica-gel fungal stocks stored at −20° C. were briefly flamed, and approximately 5 crystals were sprinkled onto the agar surface. 2-3 plates of each fungal isolate were prepared. The newly plated cultures were stored in a plastic box to prevent the cultures from drying out. FVE cultures were grown in the dark at room temperature. CGR cultures were grown in ambient light at room temperature. FGR and DMA cultures were grown in an illuminated growth chamber at 27° C. New cultures were prepared every other week to maintain a consistent supply of spores.

Spore Preparation

Spores were prepared from 2-4 week old cultures of FVE, FGR, CGR, and DMA. For FGR, FVE, and DMA, a portion of the culture plate was rinsed with a small amount of assay medium. The rinse solution was permitted to remain on the DMA plates for a time sufficient to allow the pycnidia rupture. The assay medium was then transferred to a sterile tube. Samples were vortexed, and spores were quantified using a hemacytometer.

For CGR, a sterile loop was gently dragged across orange areas of the culture plate. The loop was then inserted into a small volume of assay media, and the media was mixed with the loop to suspend the spores. Samples were vortexed, and spores were quantified using a hemacytometer.

Spores were diluted to the desired concentration with assay medium (4,000 spores per mL for FGR, FVE, and CGR, and 6,000 spores per mL for DMA) and kept on ice prior to beginning the antifungal activity assay.

Assay Plate Preparation Details

Standard non-tissue culture treated 96 well flat bottom plates or ½ area non-treated plates (Costar) were used in the antifungal plate assays. Assay medium was ¼× potato dextrose broth for FVE, FGR and DMA, and ¼×Czapec-Dox V8 was used for CGR.

Antifungal polypeptides at various concentrations were added to the plates at 50 μL/well for a standard assay plate or 25 μL/well for a half area plate. An equal volume of media with fungal spores at 2 times the above concentrations was then added to start the assay. The plates were sealed with a gas permeable membrane ("Breathe-Easy", Cat. No. BEM-1, Diversified Biotech, Boston, Mass.), and the assay was allowed to develop in the dark at 28° C. for 24 to 48 hours.

After the incubation period, the plates were placed on an inverted microscope, and each well was examined and scored to determine the IC50 of the antifungal polypeptide.

Results

Table 2 provides the results of antifungal activity assays with the defensin variants.

TABLE 2

Antifungal activity (IC50 in ppm) of defensin
variants against C. graminicola as measured under
high salt conditions.

| PDF1 protein | IC50 (ppm) |
|---|---|
| Pp-PDF1 (SEQ ID NO: 4) | 15 |
| Pp-PDF1-1C-7A4 (SEQ ID NO: 6) | 5 |
| Pp-PDF1-1C-7C4 (SEQ ID NO: 8) | 5 |
| Pp-PDF1 (C2B5) (SEQ ID NO: 10) | 0.8 |
| Pp-PDF1 (4B11) (SEQ ID NO: 12) | 1 |

Media Recipes

1× Czapek-Dox V8 Broth:

For each liter, suspend 35 grams Difco Czapek-Dox Broth (#233810) in $dH_2O$ and add 180 milliliters V8 juice that has been clarified by centrifugation (3,000×g is plenty). Raise final volume to 1 liter and autoclave at 121° C. for 20 minutes. The media is filter sterilized to remove any remaining debris.

1× Potato Dextrose Broth:

For each liter, suspend 24 grams Difco Potato Dextrose Broth (#0549-17-9) in $dH_2O$ and raise final volume to 1 liter and autoclave at 121° C. for 20 minutes. The media is filter sterilized to remove any remaining debris.

V8 Agar:

For each liter, dissolve 180 mL V8 juice and 3 grams calcium carbonate in 820 mL deionized water and then add 17 grams Bacto-agar in $dH_2O$ in a 4 liter vessel. 10 drops of 5% antifoam A may be optionally added per liter prepared. Cover and autoclave at 121° C. for 20 minutes. Pour plates in sterile hood.

Oatmeal Agar:

For each liter, suspend 36.24 grams of Difco Oatmeal Agar (#0552-17-3) and 4.25 grams agar in $dH_2O$ in a 4 liter vessel, cover and autoclave at 121° C. for 20 minutes. Pour plates in sterile hood.

| | FVE | FGR | CGR | DMA |
|---|---|---|---|---|
| Isolate name | MO33 | 73B ISU | Carroll-IA-99 | Warren-IN-96 |
| Medium for sporulation | V8 Agar | ½X Oatmeal Agar | ½X Oatmeal Agar | ½X Oatmeal Agar |
| Agar culture age range for in vitro assay | 2-4 weeks old | 2-4 weeks old | 2-4 weeks old | 2-4 weeks old |
| Suggested schedule for starting agar cultures | Every other week | Every other week | Every other week | Every other week |
| Liquid medium for in vitro assay | ¼x potato dextrose broth | ¼ x potato dextrose broth | ¼ x Czapec-Dox V8 broth | ¼x potato dextrose broth |
| Spore Density for in vitro assay (spores/mL) | 4,000 | 4,000 | 4,000 | 6,000 |

Example 3

Agrobacterium-Mediated Transformation of Maize and Regeneration of Transgenic Plants For Agrobacterium-mediated transformation of maize with a nucleotide sequence encoding the polypeptide of SEQ ID NO: 6, 8, 10, or 12, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the polynucleotide construct to at least one cell of at least one of the immature embryos (step 1: the infection step). In this step the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of Agrobacterium without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Invasion of Leaf Sheaths by C. graminicola

The leaf sheaths of leaf 4 or 5 of T0 plants at the V5 stage were inoculated with 50 µL of $5 \times 10^6$ spores/mL after wounding the leaf sheath on both sides of the midrib about half way between edge and midrib with a small screwdriver. The leaf sheath was covered with plastic wrap for 5 days. Nine days after inoculation the area of lesions was measured.

The PHP28956 plasmid comprising RB-ATTB4-E35S-UBI-BAA::Pp-PDF1(MAT)(7C4)-PINII-ATTB3+UBI-MOPAT-PINII-LB was constructed. The strong constitutive promoter E35S-UBI is present along with BAA, the signal sequence from the barley alpha-amylase in order to secrete the antifungal protein to the extracellular space. Using a Western analysis of transgenic maize calli and LC-mass spectrometry, the maize-optimized gene was expressed, resulting in accumulation of the correctly processed peptide. Westerns also demonstrated accumulation of Pp-PDF1-1C-7C4 in the leaf sheath tissue that was subjected to the infection assay. Analysis of CGR lesions indicated that the transgenics having PHP28956 had significantly smaller lesions than the empty vector control construct PHP17812.

Further, enhanced resistance of maize leaf sheaths to *C. graminicola* was observed with the following additional maize transformation constructs:

PHP28071: RB-E35S-UBI-ATTB1-BAA::Pp-PDF1(MAT)(7A4)::KDEL-ATTB2-PINII+FRT6+FRT1+E35S-35S-ADH1-BAR-PINII+FRT1-LB

PHP29782: RB-ATTB1-E35S-UBI-BAA::Pp-PDF1(MAT)(C2B5)-PINII-ATTB2+UBI-MOPAT-PINII-LB

PHP29792: RB-ATTB1-E35S-UBI-BAA::Pp-PDF1(MAT)(4B11-2)-PINII-ATTB2+UBI-MOPAT-PINII-LB.

The standard approach for AFP targeting was the use of the following components in the constructs:

the strong constitutive E35S-UBI promoter;
for secretion to the apoplast: BAA-AFP;
for ER retention: BAA-AFP-KDEL;
for vacuole targeting: BAA-AFP-CTPP;
BAA: SEQ ID NO: 14.

Other ER retention sequences are provided as SEQ ID NOs: 15, 16, 17 and 18.

CTPP: ZmPDF20-CTPP (LAAAEAEADGASQQAVATPRLN SEQ ID NO: 61) was used for vacuole-targeting; Others sequences include Cc-DFn37 CTPP (VFDNIPNDVGTILVQDAKTLEAQLLEEEILGL SEQ ID NO: 62)

Callus or Leaf Samples Expressing Php30739: E35S-Ubi-Baa-Pp-Pdf1(7A4)-ZmPDF20-CTPP or PHP30807: E35S-UBI-BAA-Pp-PDF1(7A4)-Cc-Dfn37-CTPP expressing PHP were analyzed by LCMS and showed accumulation of the correctly processed mature AFP (The BAA and the CTPP were cleaved off in the cells).

Maize was transformed with vectors designed to result in accumulation of Pp-PDF1-1C-7A4 in the endoplasmic reticulum of plant cells. In greenhouse experiments measuring the invasion of leaf sheaths of T0 V5-stage plants by CGR, two different transformation constructs resulted in significantly improved events compared to empty vector controls. Levels of Pp-PDF1-1C-7A4 protein correlated inversely with disease development.

Example 5

Transformation of Soybean Embryos

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature,* 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the antifungal protein coding sequence are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the antifungal protein coding sequence are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M $CaCl_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for fungal resistance.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

SB196—FN Lite Liquid Proliferation Medium (Per Liter)—

| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. An isolated polynucleotide comprising a nucleotide sequence selected from the group consisting of:
   (a) the nucleotide sequence set forth in SEQ ID NO: 5, 7, 9 or 11;
   (b) a nucleotide sequence encoding an amino acid sequence comprising SEQ ID NO: 6, 8, 10, or 12;
   (c) a nucleotide sequence encoding an amino acid sequence having at least 85% sequence identity to SEQ ID NO: 6, 8, 10, or 12;
   wherein said polynucleotide encodes a polypeptide having antifungal activity against *Colletotrichum graminocola*; and wherein said polypeptide has the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

2. The isolated polynucleotide of claim 1, wherein said polynucleotide encodes a polypeptide having improved antifungal activity against *Colletotrichum graminocola*, wherein the antifungal activity is improved when compared to a polypeptide comprising the amino acid sequence set forth in SEQ ID NO: 2 or 4.

3. An expression cassette comprising the polynucleotide of claim 1.

4. A host cell comprising the cassette of claim 3.

5. A microorganism comprising the expression cassette of claim 3.

6. A plant or plant part comprising a heterologous polynucleotide operably linked to a promoter that drives expression in the plant, wherein said heterologous polynucleotide comprises a nucleotide sequence selected from the group consisting of:
   (a) the nucleotide sequence set forth in SEQ ID NO: 5, 7, 9, or 11;
   (b) a nucleotide sequence encoding an amino acid sequence comprising SEQ ID NO: 6, 8, 10, or 12;
   (c) a nucleotide sequence encoding an amino acid sequence having at least 85% sequence identity to SEQ ID NO: 6, 8, 10, or 12, wherein said polynucleotide encodes a polypeptide having antifungal activity against *Colletotrichum qraminocola*;
   and wherein said polypeptide has the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

7. The plant of claim 6, wherein said polypeptide has improved antifungal activity against *Colletotrichum graminocola* when compared to a plant comprising a polypeptide comprising the amino acid sequence set forth in SEQ ID NO: 2 or 4.

8. The plant of claim 6, wherein said plant is a plant part selected from the group consisting of a cell, a seed, and a grain.

9. The plant of claim 6, wherein said plant is a monocot.

10. The plant of claim 6, wherein said plant is a dicot.

11. A method of enhancing plant pathogen resistance in a plant, said method comprising providing to said plant a polypeptide selected from the group consisting of:
   (a) a polypeptide comprising the amino acid sequence set forth in SEQ ID NO: 6, 8, 10, or 12; and
   (b) a polypeptide comprising an amino acid sequence having at least 85% sequence identity to SEQ ID NO: 6, 8, 10, or 12, wherein said polypeptide has antifungal activity against *Colletotrichum qraminocola*; and
   and wherein said polypeptide has the amino acid residues selected from the group consisting of:
   (a) the arginine (Arg) residue at the position corresponding to residue 1 of SEQ ID NO: 6, 8, 10, or 12;
   (b) the serine (Ser) residue at the position corresponding to residue 16 of SEQ ID NO: 6, 8, 10, or 12;
   (c) the arginine (Arg) residue at the position corresponding to residue 25 of SEQ ID NO: 6, 8, 10, or 12;
   (d) the serine (Ser) residue at the position corresponding to residue 36 of SEQ ID NO: 6, 8, 10, or 12; and
   (e) the serine (Ser) residue at the position corresponding to residue 42 of SEQ ID NO: 6, 8, 10, or 12.

12. An antifungal composition comprising at least one polypeptide according to claim 1.

13. The composition of claim 12 further comprising a carrier.

14. A method for protecting a plant from a pathogen, said method comprising applying the composition according to claim 12 to the environment of a plant pathogen.

15. The method of claim 14, wherein said composition is applied by a procedure selected from the group consisting of spraying, dusting, broadcasting, and seed coating.

* * * * *

SEQUENCE LISTING

<160> NUMBER OF SEQ ID NOS: 62

<210> SEQ ID NO 1
<211> LENGTH: 254
<212> TYPE: DNA
<213> ORGANISM: Picramnia pentandra

```
<220> FEATURE:
<221> NAME/KEY: misc_feature
<222> LOCATION: (1)...(254)
<223> OTHER INFORMATION: Full-length Pp-PDF1 cds

<400> SEQUENCE: 1
atggataaga aattcttcgg cctcttgctg ttggtgttca tcttatttgc tttcgaggga      60
aacatgcttc aagttgaagc aaaagtttgc accaaaccga gcaagttctt taagggttta    120
tgcggtgccg atcgtgactg tactgtagct tgtaagaagg aaggcttggc cactggattt    180
tgtcagaaaa aaggatttt taactttgtt tgcgtatgca gaaagccttg ttgaattcaa     240
taaaagaggt gtac                                                       254

<210> SEQ ID NO 2
<211> LENGTH: 77
<212> TYPE: PRT
<213> ORGANISM: Picramnia pentandra

<400> SEQUENCE: 2

Met Asp Lys Lys Phe Phe Gly Leu Leu Leu Val Phe Ile Leu Phe
 1               5                  10                  15

Ala Phe Glu Gly Asn Met Leu Gln Val Glu Ala Lys Val Cys Thr Lys
            20                  25                  30

Pro Ser Lys Phe Phe Lys Gly Leu Cys Gly Ala Asp Arg Asp Cys Thr
        35                  40                  45

Val Ala Cys Lys Lys Glu Gly Leu Ala Thr Gly Phe Cys Gln Lys Lys
    50                  55                  60

Gly Phe Phe Asn Phe Val Cys Val Cys Arg Lys Pro Cys
65                  70                  75

<210> SEQ ID NO 3
<211> LENGTH: 150
<212> TYPE: DNA
<213> ORGANISM: Picramnia pentandra
<220> FEATURE:
<221> NAME/KEY: misc_feature
<222> LOCATION: (1)...(150)
<223> OTHER INFORMATION: Mature Pp-PDF1 cds

<400> SEQUENCE: 3
aaagtttgca ccaaaccgag caagttcttt aagggtttat gcggtgccga tcgtgactgt      60
actgtagctt gtaagaagga aggcttggcc actggatttt gtcagaaaaa aggatttttt    120
aactttgttt gcgtatgcag aaagccttgt                                      150

<210> SEQ ID NO 4
<211> LENGTH: 50
<212> TYPE: PRT
<213> ORGANISM: Picramnia pentandra

<400> SEQUENCE: 4

Lys Val Cys Thr Lys Pro Ser Lys Phe Phe Lys Gly Leu Cys Gly Ala
 1               5                  10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Arg Lys
        35                  40                  45

Pro Cys
    50
```

```
<210> SEQ ID NO 5
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1 (7A4) cds

<400> SEQUENCE: 5
agggtctgcg agaagccgtc taagtttttt aaaggtttgt gtggctctga ccgcgattgt      60
acgaacgcat gtaggaaaga gggcctggcg accggcgagt gtcagtctaa gggattttc     120 aatagtgtct gcgtttgcaa aaaccttgt                                      150

<210> SEQ ID NO 6
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 6

Arg Val Cys Glu Lys Pro Ser Lys Phe Phe Lys Gly Leu Cys Gly Ser
 1               5                  10                  15

Asp Arg Asp Cys Thr Asn Ala Cys Arg Lys Glu Gly Leu Ala Thr Gly
            20                  25                  30

Glu Cys Gln Ser Lys Gly Phe Phe Asn Ser Val Cys Val Cys Lys Lys
        35                  40                  45

Pro Cys
    50

<210> SEQ ID NO 7
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1 (7C4) cds

<400> SEQUENCE: 7
cgcgtgtgca ccaagccaag caagttcttc aagggcatgt gcgtgagcga caacgattgc      60
acccatgctt gccgcaagga aggactcgct acaggcttct gccagtccaa gggattcttc     120
aattctgtgt gcgtttgcac caagccatgc                                     150

<210> SEQ ID NO 8
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 8

Arg Val Cys Thr Lys Pro Ser Lys Phe Phe Lys Gly Met Cys Val Ser
 1               5                  10                  15

Asp Asn Asp Cys Thr His Ala Cys Arg Lys Glu Gly Leu Ala Thr Gly
```

```
                    20                  25                  30
Phe Cys Gln Ser Lys Gly Phe Phe Asn Ser Val Cys Val Cys Thr Lys
         35                  40                  45
Pro Cys
    50

<210> SEQ ID NO 9
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1 (C2B5) cds

<400> SEQUENCE: 9
agggtctgcg agaagccgtc taagtttttt aaaggtatgt gtgtttctga ccgcaactgt    60
acgaacgctt gtaggaaaga gggcctgcct accggctttt gtcagtctaa ggattttttc   120
aatagtgtct gcgtttgcaa gaaaccttgt                                    150

<210> SEQ ID NO 10
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 10

Arg Val Cys Glu Lys Pro Ser Lys Phe Phe Lys Gly Met Cys Val Ser
  1               5                  10                  15

Asp Arg Asn Cys Thr Asn Ala Cys Arg Lys Glu Gly Leu Pro Thr Gly
                 20                  25                  30

Phe Cys Gln Ser Lys Gly Phe Phe Asn Ser Val Cys Val Cys Lys Lys
         35                  40                  45

Pro Cys
    50

<210> SEQ ID NO 11
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1 (4B11) cds

<400> SEQUENCE: 11
cgtgtttgca caaagccatc taagttcttc aagggcatgt gtgtaagcga caacaactgc    60
acccatgcat gccgtaagga gggcttgcct actggtttct gccagtccaa aggcttttc    120 aactccgttt gcgtttgcaa gaagccatgc                                    150

<210> SEQ ID NO 12
<211> LENGTH: 50
<212> TYPE: PRT
<213> ORGANISM: Artificial Sequence
<220> FEATURE:
```

<223> OTHER INFORMATION: Synthetic sequence obtained from DNA shuffling
      of a plant sequence.

<400> SEQUENCE: 12

Arg Val Cys Thr Lys Pro Ser Lys Phe Phe Lys Gly Met Cys Val Ser
1               5                   10                  15

Asp Asn Asn Cys Thr His Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 13
<211> LENGTH: 72
<212> TYPE: DNA
<213> ORGANISM: Artificial Sequence
<220> FEATURE:
<223> OTHER INFORMATION: Synthetic sequence for signal peptides.
<220> FEATURE:
<221> NAME/KEY: misc_feature
<222> LOCATION: (1)...(72)
<223> OTHER INFORMATION: BAA signal peptide cds

<400> SEQUENCE: 13
atggccaaca agcacctgtc cctctccctc ttcctcgtgc tcctcggcct ctccgcctcc    60
ctcgcctccg ga                                                        72

<210> SEQ ID NO 14
<211> LENGTH: 24
<212> TYPE: PRT
<213> ORGANISM: Artificial Sequence
<220> FEATURE:
<223> OTHER INFORMATION: Synthetic sequence for signal peptides.

<400> SEQUENCE: 14

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 15
<211> LENGTH: 4
<212> TYPE: PRT
<213> ORGANISM: Artificial Sequence
<220> FEATURE:
<223> OTHER INFORMATION: Synthetic ER retention sequence

<400> SEQUENCE: 15

Lys Asp Glu Leu
1

<210> SEQ ID NO 16
<211> LENGTH: 6
<212> TYPE: PRT
<213> ORGANISM: Artificial Sequence
<220> FEATURE:
<223> OTHER INFORMATION: Synthetic ER retention sequence.

<400> SEQUENCE: 16

Ser Glu Lys Asp Glu Leu
1               5

<210> SEQ ID NO 17

```
<211> LENGTH: 4
<212> TYPE: PRT
<213> ORGANISM: Artificial Sequence
<220> FEATURE:
<223> OTHER INFORMATION: Synthetic ER retention sequence.

<400> SEQUENCE: 17

His Asp Glu Leu
 1

<210> SEQ ID NO 18
<211> LENGTH: 4
<212> TYPE: PRT
<213> ORGANISM: Artificial Sequence
<220> FEATURE:
<223> OTHER INFORMATION: Synthetic ER retention sequence.

<400> SEQUENCE: 18

His Asp Glu Phe
 1

<210> SEQ ID NO 19
<211> LENGTH: 81
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(81)
<223> OTHER INFORMATION: Propeptide of Pp-PDF1 cds

<400> SEQUENCE: 19
atggataaga aattcttcgg cctcttgctg ttggtgttca tcttatttgc tttcgaggga      60
aacatgcttc aagttgaagc a                                               81

<210> SEQ ID NO 20
<211> LENGTH: 27
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 20

Met Asp Lys Lys Phe Phe Gly Leu Leu Leu Leu Val Phe Ile Leu Phe
 1               5                  10                  15

Ala Phe Glu Gly Asn Met Leu Gln Val Glu Ala
            20                  25

<210> SEQ ID NO 21
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-1C-7C4 cds

<400> SEQUENCE: 21
agggtctgca caaagccgtc taagtttttt aaaggtatgt gtgtttctga caatgattgt      60
acgcacgctt gtaggaaaga gggcctggcg accggctttt gtcagtctaa gggattttc     120
```

```
aatagtgtct gcgtttgcac aaaaccttgt                                      150
```

<210> SEQ ID NO 22
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-1C-6D3 cds

<400> SEQUENCE: 22

```
agggtctgcg agaagccgtc taagttttt aaaggtttgt gtgttaggga ccgcgattgt       60
gcggtcgcat gtaagaaaga gggcctggcg tcaggctttt gtcagtctaa gggattttc     120 aatagtgtct gcgtttgcaa aaaaccttgt                                      150
```

<210> SEQ ID NO 23
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 23

```
Arg Val Cys Glu Lys Pro Ser Lys Phe Phe Lys Gly Leu Cys Val Arg
 1               5                  10                  15

Asp Arg Asp Cys Ala Val Ala Cys Lys Lys Glu Gly Leu Ala Ser Gly
            20                  25                  30

Phe Cys Gln Ser Lys Gly Phe Phe Asn Ser Val Cys Val Cys Lys Lys
        35                  40                  45

Pro Cys
    50
```

<210> SEQ ID NO 24
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-1F-1C5 cds

<400> SEQUENCE: 24

```
aaggtctgca caaagccgtc taagttttt aaaggtatgt gtgtcaggga ccgcgattgt       60
acgaacgcat gtaggaaaga gggcctggcg tctggctttt gtcagaagaa gggattttc     120 aattttgtct gcgtttgcag aaaaccttgt                                      150
```

<210> SEQ ID NO 25
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 25

```
Lys Val Cys Thr Lys Pro Ser Lys Phe Phe Lys Gly Met Cys Val Arg
```

```
                1               5                      10                      15
              Asp Arg Asp Cys Thr Asn Ala Cys Arg Lys Glu Gly Leu Ala Ser Gly
                              20                  25                  30

Phe Cys Gln Lys Lys Gly Phe Phe Asn Phe Val Cys Val Cys Arg Lys
                      35                  40                  45

Pro Cys
                  50

<210> SEQ ID NO 26
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-1F-12H3 cds

<400> SEQUENCE: 26
agggtctgca caaagccgtc taagttttttt aaaggtttgt gtgtctctga cgatgattgt        60
gcgcacgcat gtaggaaaga gggcctggcg acgggcaagt gtcagaagaa gggattttttc      120 aatagggtct gcgtttgcaa aaaaccttgt                                         150

<210> SEQ ID NO 27
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 27

Arg Val Cys Thr Lys Pro Ser Lys Phe Phe Lys Gly Leu Cys Val Ser
                1               5                      10                      15

Asp Asp Asp Cys Ala His Ala Cys Arg Lys Glu Gly Leu Ala Thr Gly
                              20                  25                  30

Lys Cys Gln Lys Lys Gly Phe Phe Asn Arg Val Cys Val Cys Lys Lys
                      35                  40                  45

Pro Cys
                  50

<210> SEQ ID NO 28
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-1F-7H6 cds

<400> SEQUENCE: 28
agggtctgcg agaagccgtc taagttttttt aaaggtatgt gtgtcaggga ccgcgattgt        60
acggtcgcat gtaagaaaga gggcctggcg acaggctttt gtcagaagaa gggattttttc      120 aattttgtct gcgtttgcaa aaaaccttgt                                         150

<210> SEQ ID NO 29
<211> LENGTH: 50
```

```
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 29

Arg Val Cys Glu Lys Pro Ser Lys Phe Phe Lys Gly Met Cys Val Arg
 1               5                  10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Lys Lys
        35                  40                  45

Pro Cys
    50

<210> SEQ ID NO 30
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-2CA-1A6 cds

<400> SEQUENCE: 30
agggtctgca agaagccgtc taagtttttt aaaggtttgt gtctgtcgga ccgcgattgt      60
acgaacgcat gtaggaaaga gggcctggcg accggcgagt gtcagtctaa gggatttttc    120
aatagtgtct gcgtttgcag aaaaccatgt                                     150

<210> SEQ ID NO 31
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 31

Arg Val Cys Lys Lys Pro Ser Lys Phe Phe Lys Gly Leu Cys Leu Ser
 1               5                  10                  15

Asp Arg Asp Cys Thr Asn Ala Cys Arg Lys Glu Gly Leu Ala Thr Gly
            20                  25                  30

Glu Cys Gln Ser Lys Gly Phe Phe Asn Ser Val Cys Val Cys Arg Lys
        35                  40                  45

Pro Cys
    50

<210> SEQ ID NO 32
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-2CE-4A7 cds

<400> SEQUENCE: 32
```
cgtgtttgca caaagccatc taagttcttc aagggcctgt gtgtaagcga caacaactgc    60
acccatgcat gccgtacgga gggcttgcct attggtttct gccagtccaa aggcttttc    120 aactccgttt gcgtttgcaa gaagccatgc    150

<210> SEQ ID NO 33
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 33

Arg Val Cys Thr Lys Pro Ser Lys Phe Phe Lys Gly Leu Cys Val Ser
1               5                   10                  15

Asp Asn Asn Cys Thr His Ala Cys Arg Thr Glu Gly Leu Pro Ile Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 34
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-2CA-1H4 cds

<400> SEQUENCE: 34
agggtctgcc gtaagccgtc taagtttttt aaaggtttgt gtctgtcgga ccgcgattgt    60
acgaacgcat gtaggaaaga gggcctggcg accggcgagt gtcagtctaa gggattttc    120 aatagtgtct gcgtttgcga aaaaccatgt    150

<210> SEQ ID NO 35
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 35

Arg Val Cys Arg Lys Pro Ser Lys Phe Phe Lys Gly Leu Cys Leu Ser
1               5                   10                  15

Asp Arg Asp Cys Thr Asn Ala Cys Arg Lys Glu Gly Leu Ala Thr Gly
            20                  25                  30

Glu Cys Gln Ser Lys Gly Phe Phe Asn Ser Val Cys Val Cys Glu Lys
        35                  40                  45

Pro Cys
    50

<210> SEQ ID NO 36
<211> LENGTH: 150
<212> TYPE: DNA
<213> ORGANISM: Artificial Sequence
<220> FEATURE:

<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-2CA-5H4 cds

<400> SEQUENCE: 36
agggtctgca agaagccgtc taagttttt aaaggtttgt gtctgtcgga ccgcgattgt    60
acgaacgcat gtaggaaaga gggcctggcg accggcgagt gtcagtctaa ggatttttc   120 aatagtgtct gcgtttgcga aaaccatgt                                    150

<210> SEQ ID NO 37
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 37

Arg Val Cys Lys Lys Pro Ser Lys Phe Phe Lys Gly Leu Cys Leu Ser
1               5                   10                  15

Asp Arg Asp Cys Thr Asn Ala Cys Arg Lys Glu Gly Leu Ala Thr Gly
            20                  25                  30

Glu Cys Gln Ser Lys Gly Phe Phe Asn Ser Val Cys Val Cys Glu Lys
        35                  40                  45

Pro Cys
    50

<210> SEQ ID NO 38
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-2CF-2D8 cds

<400> SEQUENCE: 38
cgtgtctgca ctaaaccatc caaattctat aaaggcctgt gcgtaagcga tagggattgc    60
actaacgcgt gccgtaagga aggcttgcct actgggtttt gccaatccaa aggcttcttc   120
aattctgttt gtgtttgtaa gaaaccatgc                                   150

<210> SEQ ID NO 39
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 39

Arg Val Cys Thr Lys Pro Ser Lys Phe Tyr Lys Gly Leu Cys Val Ser
1               5                   10                  15

Asp Arg Asp Cys Thr Asn Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 40
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-2CF-10F3 cds

<400> SEQUENCE: 40
cgtgtctgca ctaaaccatc caaattcttt agaggcctgt gcgtaagcga taggaattgc     60
actaacgcgt gccgtaagga aggcttgcct actggggaat gcaaatccaa aggcttcttc    120
aattctgttt gtgtttgtaa gaaaccatgc                                     150

<210> SEQ ID NO 41
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 41

Arg Val Cys Thr Lys Pro Ser Lys Phe Phe Arg Gly Leu Cys Val Ser
  1               5                  10                  15

Asp Arg Asn Cys Thr Asn Ala Cys Arg Lys Glu Gly Leu Pro Thr Gly
                 20                  25                  30

Glu Cys Lys Ser Lys Gly Phe Phe Asn Ser Val Cys Val Cys Lys Lys
             35                  40                  45

Pro Cys
    50

<210> SEQ ID NO 42
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-3CA-1A2 cds

<400> SEQUENCE: 42
cgcgtgtgca ccaaaccgag caaattttac cgtggtctgt gcgtttctga ccgtgactgc     60
acccatgcct gtcgcaagga aggcctgccg accggcttct gccagtctaa gggtttcttc    120
aactccgttt gcgtctgcaa aaaaccgtgt                                     150

<210> SEQ ID NO 43
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 43

```
Arg Val Cys Thr Lys Pro Ser Lys Phe Tyr Arg Gly Leu Cys Val Ser
 1               5                  10                  15

Asp Arg Asp Cys Thr His Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 44
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-3CA-1A7 cds

<400> SEQUENCE: 44
cgcgtgtgca ccaaaccgag caaattttc cgtggtctgt gcgtttctga ccgtgactgc      60
accaatgcct gtcgcaagga aggcctgccg atcggcttct gccagtctaa gggtttcttc     120
aactccgttt gcgtctgcaa aaaccgtgt                                      150

<210> SEQ ID NO 45
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 45

Arg Val Cys Thr Lys Pro Ser Lys Phe Phe Arg Gly Leu Cys Val Ser
 1               5                  10                  15

Asp Arg Asp Cys Thr Asn Ala Cys Arg Lys Glu Gly Leu Pro Ile Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 46
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-3CA-1B2 cds

<400> SEQUENCE: 46
cgcgtgtgca ccaaaccgag caaattttac cgtggtctgt gcgtttctga ccgtgactgc      60
acccatgcct gtcgcaagga aggcctgccg atcggcgaat gcaagtctaa gggtttcttc     120
aactccgttt gcgtctgcaa aaaccgtgt                                      150

<210> SEQ ID NO 47
```

```
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 47

Arg Val Cys Thr Lys Pro Ser Lys Phe Tyr Arg Gly Leu Cys Val Ser
1               5                   10                  15

Asp Arg Asp Cys Thr His Ala Cys Arg Lys Glu Gly Leu Pro Ile Gly
            20                  25                  30

Glu Cys Lys Ser Lys Gly Phe Phe Asn Ser Val Cys Val Cys Lys Lys
        35                  40                  45

Pro Cys
    50

<210> SEQ ID NO 48
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-3CA-1E6 cds

<400> SEQUENCE: 48
cgcgtgtgca ccaaaccgag caaattttac cgtggtctgt gcgtttctga ccgtgactgc    60
accaatgcct gtcgcaagga aggcctgccg accggcttct gccagtctaa gggtttcttc   120
aactccgttt gcgtctgcaa aaaccgtgt                                      150

<210> SEQ ID NO 49
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 49

Arg Val Cys Thr Lys Pro Ser Lys Phe Tyr Arg Gly Leu Cys Val Ser
1               5                   10                  15

Asp Arg Asp Cys Thr Asn Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 50
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-3CA-2D3 cds

<400> SEQUENCE: 50
```

```
cgcgtgtgca ccaaaccgag caaattttc cgtggtctgt gcgtttctga caatgactgc    60
accaatgcct gtcgcaagga aggcctgccg accggcttct gccagtctaa gggtttcttc   120
aactccgttt gcgtctgcaa aaaccgtgt                                     150
```

```
<210> SEQ ID NO 51
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 51
```

Arg Val Cys Thr Lys Pro Ser Lys Phe Phe Arg Gly Leu Cys Val Ser
1               5                   10                  15

Asp Asn Asp Cys Thr Asn Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

```
<210> SEQ ID NO 52
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-4CB-6E6 cds

<400> SEQUENCE: 52
```

```
cgtgtctgca ctaaaccatc caaattctat aagggcctgt gcatctctga tcgtgactgc    60
actaacgcgt gccgtaagga aggcttgcct attgggtttt gcaagtctaa aggcttcttc   120
aattctgttt gtgtttgtcg caaaccatgc                                    150
```

```
<210> SEQ ID NO 53
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 53
```

Arg Val Cys Thr Lys Pro Ser Lys Phe Tyr Lys Gly Leu Cys Ile Ser
1               5                   10                  15

Asp Arg Asp Cys Thr Asn Ala Cys Arg Lys Glu Gly Leu Pro Ile Gly
            20                  25                  30

Phe Cys Lys Ser Lys Gly Phe Phe Asn Ser Val Cys Val Cys Arg Lys
        35                  40                  45

Pro Cys
    50

```
<210> SEQ ID NO 54
<211> LENGTH: 150
<212> TYPE: DNA
<213> ORGANISM: Artificial Sequence
```

```
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-4CB-6E9 cds

<400> SEQUENCE: 54
cgtgtctgca ctaaaccatc caaattcttt aagggcctgt gcatctctga tcgtcaatgc    60
actaacgcgt gccgtaagga aggcttgcct actggggaat gccagcctaa aggcttcttc   120
aattctgttt gtgtttgtcg caaaccatgc                                    150

<210> SEQ ID NO 55
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 55

Arg Val Cys Thr Lys Pro Ser Lys Phe Phe Lys Gly Leu Cys Ile Ser
  1               5                  10                  15

Asp Arg Gln Cys Thr Asn Ala Cys Arg Lys Glu Gly Leu Pro Thr Gly
             20                  25                  30

Glu Cys Gln Pro Lys Gly Phe Phe Asn Ser Val Cys Val Cys Arg Lys
         35                  40                  45

Pro Cys
     50

<210> SEQ ID NO 56
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: Pp-PDF1-4CB-12G9 cds

<400> SEQUENCE: 56
cgtgtctgca ctaaaccatc caaattcttt cgtggcctgt gcgtctctga tcgtcaatgc    60
actaacgcgt gccgtaagga aggcttgcct attggggaat gccagtctaa aggcttcttc   120
aattctgttt gtgtttgtcg caaaccatgc                                    150

<210> SEQ ID NO 57
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 57

Arg Val Cys Thr Lys Pro Ser Lys Phe Phe Arg Gly Leu Cys Val Ser
  1               5                  10                  15

Asp Arg Gln Cys Thr Asn Ala Cys Arg Lys Glu Gly Leu Pro Ile Gly
             20                  25                  30

Glu Cys Gln Ser Lys Gly Phe Phe Asn Ser Val Cys Val Cys Arg Lys
         35                  40                  45
```

Pro Cys
    50

<210> SEQ ID NO 58
<211> LENGTH: 150
<212> TYPE: DNA
<213> ORGANISM: Artificial Sequence
<220> FEATURE:
<223> OTHER INFORMATION: Synthetic sequence obtained from DNA shuffling
      of a plant sequence.
<220> FEATURE:
<221> NAME/KEY: misc_feature
<222> LOCATION: (1)...(150)
<223> OTHER INFORMATION: PP-PDF1-2CE-41G2 cds

<400> SEQUENCE: 58
cgtgtttgca caaagccatc taagttcttc aagggcatgt gtgtaagcga caacaactgc     60
acccatgcat gccgtaagga gggcttgcct actggtttct gccagtccaa aggcttttc    120 aactccgttt gcgtttgcaa gaagccatgc                                    150

<210> SEQ ID NO 59
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.

<400> SEQUENCE: 59

Arg Val Cys Thr Lys Pro Ser Lys Phe Phe Lys Gly Met Cys Val Ser
 1               5                  10                  15

Asp Asn Asn Cys Thr His Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 60
<211> LENGTH: 50
<212> TYPE: PRT
<213> ORGANISM: Artificial Sequence
<220> FEATURE:
<223> OTHER INFORMATION: Synthetic sequence obtained from DNA shuffling
      of a plant sequence.  Consensus sequence from
      alignment.

<400> SEQUENCE: 60

Arg Val Cys Thr Lys Pro Ser Lys Phe Phe Lys Gly Leu Cys Val Ser
 1               5                  10                  15

Asp Arg Asp Cys Thr Asn Ala Cys Arg Lys Glu Gly Leu Pro Thr Gly
            20                  25                  30

Phe Cys Gln Ser Lys Gly Phe Phe Asn Ser Val Cys Val Cys Lys Lys
        35                  40                  45

Pro Cys
    50

<210> SEQ ID NO 61
<211> LENGTH: 22
<212> TYPE: PRT
<213> ORGANISM: Zea mays

<400> SEQUENCE: 61

```
Leu Ala Ala Ala Glu Ala Glu Ala Asp Gly Ala Ser Gln Gln Ala Val
1               5                   10                  15

Ala Thr Pro Arg Leu Asn
            20

<210> SEQ ID NO 62
<211> LENGTH: 32
<212> TYPE: PRT
<213> ORGANISM: Capsicum chinense

<400> SEQUENCE: 62

Val Phe Asp Asn Ile Pro Asn Asp Val Gly Thr Ile Leu Val Gln Asp
1               5                   10                  15

Ala Lys Thr Leu Glu Ala Gln Leu Leu Glu Glu Glu Ile Leu Gly Leu
            20                  25                  30
```